(12) United States Patent
Harbury et al.

(10) Patent No.: US 7,288,382 B2
(45) Date of Patent: Oct. 30, 2007

(54) METHODS FOR STRUCTURAL ANALYSIS OF PROTEINS

(75) Inventors: Pehr A. B. Harbury, Stanford, CA (US); Joshua A. Silverman, Redwood City, CA (US); Warham Lance Martin, Pacifica, CA (US)

(73) Assignee: The Board of Trustees od the Leland Stanford Junior University, Palo Alto, CA (US)

( * ) Notice: Subject to any disclaimer, the term of this patent is extended or adjusted under 35 U.S.C. 154(b) by 441 days.

(21) Appl. No.: 10/388,963

(22) Filed: Mar. 14, 2003

(65) Prior Publication Data

US 2003/0224448 A1 Dec. 4, 2003

Related U.S. Application Data

(60) Provisional application No. 60/365,248, filed on Mar. 14, 2002.

(51) Int. Cl.
*G01N 33/53* (2006.01)
*C12P 21/02* (2006.01)
*C12N 5/06* (2006.01)
*C07K 14/435* (2006.01)

(52) U.S. Cl. .................. 435/7.1; 435/69.1; 435/320.1; 435/325; 530/350

(58) Field of Classification Search ................ 435/7.1, 435/69.1, 320.1, 325; 530/350
See application file for complete search history.

(56) References Cited

FOREIGN PATENT DOCUMENTS

WO    WO 00/11208    3/2000
WO    WO 00/24922    5/2000

OTHER PUBLICATIONS

Doring Volker et al.Reassigning Cysteine in the Genetic code of *Escherichia coli* 1998 Genetics 150:543-551.*
Karlin et al Sustituted cysteine accessibility Method 1998. Methods in Enzymology 293: 123-145.*
Baudouin-Cornu, P., Molecular Evolution of Protein Atomic Composition, Science, 2001, 293: 297-300.
Doring, V., Enlarging the Amino Acid Set of *Escherichia coli* by Infiltration of the Valine Coding Pathway, Science, 2001, 292: 501-504.
Doring, V., Reassigning Cysteine in the Genetic Code of *Escherichia coli*, Genetics, 1998, 150: 543-551.
Doering, D.S., Cysteine Scanning Mutagensis at 40 of 76 Positions in Villin Headpiece Maps the F-Actin Binding Site and Structural Features of the Domain, Biochemistry, 1996, 35: 12677-12685.
Gygi, S. P. et al., Quantitative Analysis of Complex Protein Mixtures Using Isotope-Coded Affinity Tags, Nature Biotechnology, 1999, 17: 994-999.
Ha, J. et al., Changes in Side Chain Packing During Apomyoglobin Folding Characterized by Pulsed Thioldisulfide Exchange, Nature Structural Biology, 1998, 5(8): 730-737.
Lampert et al., Properties of the Mutant SER-460-CYS Implicate This Site in a Functionally Important Region of the Type IIa Na+/$P_i$ Cotransporter Protein, J. Gen. Physiol., 1999, 114: 637-651.
Liu, X. et al., Boronate Affinity Chromatography, Methods. Mol. Biol., 2000, 147: 119-28.
Roche, E.D., SSRA-Mediated Peptide Tagging Caused by Rare Condons and TRNA Scarcity, Embo J., 1999, 18(16): 4579-4589.
Sullivan et al., Mapping The Agonist Binding Site of the Nicotinic Acetylcholine Receptor. Orientation Requirements for Activation by Covalent Agonist, J. Biol. Chem., 2000, 275(17): 12651-60.
Tu, B. et al., Protein Footprinting at Cysteines: Probing ATP-Modulated Contacts in Cysteine-Substitution Mutants of Yeast DNA Topoisomerase II, 1999, Proc. Natl. Acad. Sci., 96: 4862-7.
Venkatesan et al., Site-Directed Site-Directed Sulfhydryl Labeling of the Lactose Permease of *Escherichia coli*: Helix X., Biochemistry, 2000, 39: 10656-10661.
Venkatesan et al., Site-Directed Site-Directed Sulfhydryl Labeling of the Lactose Permease of *Escherichia coli*: N-Ethylmaleimide-Sensitive Face of Helix II, Biochemistry, 2000, 39: 10649-10655.
Venkatesan et al., Site-Directed Sulfhydryl Labeling of the Lactose Permease of *Escherichia coli*: Helix VII, 2000, Biochemistry, 39: 10641-10648.

* cited by examiner

*Primary Examiner*—Kathleen Kerr Bragdon
*Assistant Examiner*—Kagnew Gebreyesus
(74) *Attorney, Agent, or Firm*—Bozicevic, Field & Francis LLP; James S. Keddie; Carole L. Francis

(57) ABSTRACT

The invention provides methods and compositions for protein structure analysis, including substrate binding sites, sites of protein-protein interactions, three dimensional structure analysis, and stability, all with single amino acid resolution. In general, the subject methods involve introduction of cysteine residues, which serve as probes for physical analysis, into a protein by translational misincorporation in vivo. In many embodiments, proteins containing misincorporated cysteine residues are reacted with a crosslinking agent that covalently links misincorporated cysteine residues to a proximal amino acid in the folded protein. These methods, termed "MXLINK" methods, may be used for protein tertiary structure analysis. In other embodiments, cysteine-misincorporated proteins are used in protein footprinting methods, termed "MPAX" or "MSX" methods.

13 Claims, 17 Drawing Sheets a b c

METHODS FOR STRUCTURAL ANALYSIS OF PROTEINS

FIELD OF THE INVENTION

The present invention relates to the field of protein analysis, structural analysis and topology mapping.

BACKGROUND OF THE INVENTION

In the last decade, the genomes of over 50 organisms have been sequenced, resulting in a vast increase in the number of known proteins. Characterization of the abundance, post-translational modification, structure, and function of these proteins represents a major challenge for genomic analysis. Understanding protein conformation, interactions and ligand binding is essential to all biological inquiry. Defining protein structure in molecular detail constitutes a particularly difficult task. Accurate measurement of these properties currently requires high-resolution physical methods. While X-ray crystallographic and nuclear magnetic resonance techniques are extremely powerful, they require large investments of time and material, and are limited in their application to large protein complexes, membrane proteins and other insoluble or partially folded polypeptides. Many proteins and protein complexes prove unsuitable for NMR and X-ray work. In order to rapidly obtain functional information for a large number of sequences, a general and efficient tool for probing protein conformation is required.

In principle, protein footprinting is an option for studying protein structure, but it has been far less successful than the corresponding techniques developed for nucleic acids (Galas D. J., A. Schmitz, *Nucleic Acids Res.* 5, 3157 (1978)). Conventional protein footprinting involves the treatment of a protein of interest with an enzymatic protease which cleaves the protein backbone at accessible positions. The protein fragments generated under various conditions are analyzed (e.g. in the presence or absence of substrate or ligand) to determine which regions of the protein have changed their susceptibility to the protease. Because of the chemical heterogeneity of the amino-acid side chains, no reagent (chemical or enzyme) exists with the ability to cleave the protein backbone uniformly under native conditions. Furthermore, protein separation techniques such as SDS-PAGE do not provide the single-monomer resolution of the urea-acrylamide gels used for the separation of nucleic acids, thus complicating the analysis of observed cleavage patterns. Finally, because of the cooperative nature of protein unfolding, proteolytic cleavage at one site often leads to a global loss of structure and to increased cleavage at other sites in the same molecule, resulting in artifactual data.

Footprinting by chemical modification of amino acid side chains represents a different approach to the problem. Modification of side chains is carried out under native conditions, while detection of modifications can be performed under arbitrary conditions. The susceptibility of each side chain to modification reports its solvent accessibility. Acylation of lysine residues (Doonan S., H. M. Fahmy, *Eur. J. Biochem.* 56,421, 1975); Hanai, R., J. C. Wang, *Proc. Natl. Acad. Sci. U.S.A.* 91, 11904, 1994), oxidation of methionine residues (de Arruda, M. V. et. al., *J. Biol. Chem.* 267, 13079, 1992), and alkylation of cysteine residues (Doering, D. S., P. Matsudaira, *Biochemistry* 35, 12677, 1996; Tu, B. P., J. C. Wang, *Proc. Natl. Acad. Sci. U.S.A.* 96, 4862, 1999) have been used previously to footprint protein structures. In general, these studies have been limited in scope, however, as they examine only a few naturally-occurring residues, or require extensive site-directed mutagenesis to introduce additional structural probes.

Thus, there is a need to develop a method for protein analysis which allows for the rapid structural characterization of proteins and protein complexes at a large number of sites distributed throughout the protein.

Literature of Interest

Ha and Loh (Nat. Struct. Biol., 1998. 5:730-7) and Young, et al. (Proc Natl Acad Sci USA, 2000 97: p. 5802-6) may also be of interest.

SUMMARY OF THE INVENTION

The invention provides methods and compositions for protein structure analysis, including the rapid mapping of sites of ligand binding, protein-protein interaction, and protein topology and three dimensional structure, all with single amino acid resolution. The protein footprinting method of the invention is generally referred to as the "misincorporation proton-alkyl exchange" (MPAX) method, and can be applied to large protein complexes, membrane proteins, and partially disordered polypeptides that are not amenable to study by other techniques. The methods of the invention involves introduction of cysteine residues by translational misincorporation in vivo. The misincorporated cysteines then serve as targets for modification, and thus as probes for physical analysis. The method of the invention can facilitate accurate determination of substrate binding sites, protein-protein interaction sites, protein three dimensional structure and protein stability.

A variation of the invention provides methods and compositions for measuring pairwise amino acid residue proximity using translational misincorporation of cysteines in vivo. In these methods, termed "misincorporation cross-linking" (MXLINK) methods, a protein is made with misincorporated cysteines, and intramolecular crosslinkers are used to covalently link the misincorporated cysteines to adjacent residues in the folded protein. In most embodiments, the crosslinked protein is subjected to proteolysis and the crosslinked peptides are analyzed, for example, using mass spectrometry to determine the adjacent amino acids that are crosslinked. Once determined, the proximity measurements may be used to determine the three dimensional structure of a protein. The MXLINK method is particulary suitable for proteins in complex mixtures, for determining the structure of proteins that are difficult to crystallize, too large for NMR or not suitable for other analytical methods, and in high throughput structural genomics.

In some embodiments of the above MXLINK method, crosslinkers are used to crosslink intermolecularly, e.g., between two proteins. In these embodiments, a first protein contains misincorporated cysteines is crosslinked to another protein. After subsequent proteolysis and analysis, the information may be used to map the interaction surface of the first protein.

In one aspect, the invention features a method for analysis of protein structure, the method comprising producing a cysteine-modified protein by co-expression of a mutant cysteine tRNA and a protein of interest in a recombinant host cell. The tRNA facilitates specific misincorporation of the amino acid cysteine in place of a selected amino acid other than cysteine, where the amino acid to be replaced is determined by selection of the anti-codon sequence of the cysteine misincorporator tRNA. Co-expression thus results in production of a protein having at least one non-native cysteine residue. The cysteine modified protein is then folded, and the folded cysteine-modified protein contacted with a cysteine-reactive compound under conditions suitable for modification of a solvent accessible cysteine residue in the cysteine-modified protein. Modification of a cysteine residue by the cysteine-reactive compound indicates that the chemically modified cysteine residue is solvent accessible (and thus is present at or near the surface of the folded protein). Residues that are "buried" within the folded protein are less solvent accessible, and thus chemically modified at a lower rate than the solvent accessible cysteine residues.

In related embodiments, a polynucleotide encoding a cysteine tRNA synthetase is co-expressed with the polynucleotides encoding the protein of interest and the misincorporator tRNA. In other related embodiments, the polynucleotide sequence encoding the protein of interest is modified to remove or replace native cysteine residues. In other related embodiments, the cysteine-reactive compounds include, but are not necessarily limited to, compounds that include a sulfhydryl reactive portion or moiety, and a labeling portion or moiety. The sulfhydryl reactive portion may comprise, for example, a haloalkyl group or like functional group capable of forming a carbon-sulfur bond, a sulfur-sulfur bond, or other covalent bond with a cysteine sulfhydryl group. In certain embodiments, as described further below, the sulfhydryl reactive portion may comprise a haloalkyl acyl group such as iodoacetamide, a maleimide a thiosulfonyl, or other sulfhydryl reactive group. The labeling portion of the cysteine reactive compound may comprise any labeling group or species that is detectable optically (including spectroscopically), radiometrically, magnetically, or by other detection technique. The labeling portion may thus comprise an isotopic label having present one or more detectable isotopic labels of, for example, carbon, hydrogen, sulfur, fluorine, phosphorus, or other radioactive labeling element used in the art. The labeling portion may also comprise a fluorescent label that is spectroscopically detectable.

In further related embodiments, the method further comprises contacting the sulfhydryl-reacted, cysteine-modified protein with a proteolytic agent to produce polypeptide fragments of the cysteine-modified protein, and analyzing the polypeptide fragments to determine the extent of reaction of cysteines in the protein with the sulfhydryl-reactive agent. In still other related embodiments, the time of contact of the sulfhydryl-reactive compound is varied to determine the chemical rate of reaction of cysteines in the protein. In further related embodiments, a protection factor is calculated for a cysteine residue by dividing the intrinsic rate of reaction of the cysteine residue by the observed rate reaction of the cysteine residue, which protection factor is determinative of solvent accessibility of the cysteine residue. In still further related embodiments, a model of the structure of the native protein is deduced from analysis of the solvent accessibility or proximity of native and non-native cysteine residues in one or more, usually two or more cysteine-modified proteins, more usually ten or more cysteine-modified proteins, up to a number of cysteine-modified proteins commensurate with the number of amino acid residues in the native protein.

In other related embodiments, the solvent accessibility of the chemically-modified cysteine is compared in the presence and absence of a molecule that binds the native protein (e.g., a ligand, a protein binding partner, and the like) to identify the amino acid residues on the interface of the protein or to identify amino acid residues residing within regions of the protein that undergo conformational change in the presence or absence of the molecule. In still further embodiments, the solvent accessibility of the cysteine is compared under changing the environmental conditions (e.g., temperature, pH, presence or absence of denaturant, and the like) to identify amino acid residues that are involved in regions of the protein that undergo conformational change under such environmental condition. In more embodiments, the dependence of the solvent accessibility of the cysteine on the environmental change is used to determine the stability of regions of the protein.

In some embodiments, as mentioned above, the method comprises contacting the cysteine-modified protein with a suitable crosslinker in order to study the structure of the protein or the intermolecular interaction surface of the protein. In these embodiments, the crosslinker contains cysteine-reactive moiety, also contains an affinity tag, and a crosslinking group. In many embodiments, the crosslinker is covalently linked to a cysteine of a cysteine-modified protein usually through alkylation or disulphide bond formation using, for example an α-halo amide and the crosslinker becomes covalently bound to a nearby amino acid through the its crosslinking moiety. After crosslinking has occurred, the protein is usually subjected to proteolysis using a suitable enzymatic or chemical protease, and the crosslinked peptide fragments are usually purified from other peptide fragments using, for example, an affinity tag that is part of the crosslinker and analyzed by mass spectrometry.

In other embodiments related to MPAX, cysteine-modified proteins are reacted with thiosulfonate reagents instead of iodoacetamine reagents, allowing very rapid protein modification to occur through disulfide bond formation. These MPAX-related methods are termed "misincorporation thiol exchange" (MSX) methods. In these embodiments, cysteine-modified proteins are reacted with thiosulfonate reagents in continuous pulse and delayed pulse protocols using a quench-flow device. In some embodiments, the extent of alkylation of each misincorporated cysteine will be reflected by the fractional loss of detectable label in a gel. In other embodiments, $^{13}C$-labeled and $^{12}C$-labeled-reagents are used and detected by mass spectrometry. Following mixing, the proteins are prepared for analysis and analyzed according to MPAX methods, and are identified by their mass and fragmentation pattern. The extent of alkylation of each misincorporated cysteine will be reflected by the $^{13}C/^{12}C$ ratio in the corresponding peptide product. MSX methods may be used to analyze, for example, the kinetics of protein conformational change.

In other embodiments, the proteolytic agent used to produce polypeptide fragments of the protein is an enzyme, or is a chemical proteolytic compound. Exemplary chemical proteolytic compounds include 2-nitro-5-thiocyanobenzoic acid (NTCB).

In other embodiments, the method further comprises analysis of the polypeptide fragments by, for example, gel electrophoresis or mass spectrometry.

In another embodiment, the method of the invention further comprises contacting the cysteine-modified protein with a first cysteine reactive agent under a first condition, removing unreacted first agent, and contacting the cysteine-modified protein with a second cysteine-reactive agent under a second condition, wherein the first and second agents are detectably and differentially labeled. The ratio of cysteine residues in the cysteine-modified protein that are chemically modified with the first agent to the cysteine residues that are chemically modified by the second agent is indicative of the solvent accessibility of the cysteine under the first condition relative to the second condition. The first and second conditions can differ in, for example, time allowed for access of the reactive agent solution to reach and react with cysteine residues, the presence or absence of ligand or other molecule that binds or interacts with the protein, or changes in an environmental condition (e.g., temperature, and the like).

In a related embodiment, the first cysteine-reactive agent includes a first cysteine reactive group and the second cysteine-reactive agent includes second cysteine reactive group, wherein the first and second cysteine reactive groups can be differentially and detectably labeled e.g., by virtue of an isotope label (e.g., $^{13}C$ and $^{12}C$, $^1H$ and deuterium, and the like). It should be readily understood, however, that non-isotopic labels, such as fluorescent labels, may be used in other embodiments of the invention.

In another aspect, the invention features compositions containing a compound having three functional groups, X, Y and R, which can be arranged in the compound in any suitable way (e.g. linearly e.g. X—Y—R, Y—X—R or Y—R—X, as branches from a backbone molecule, or joined to a linking molecule, such as a nitrogen etc.). One suitable arrangement of a compound is:

In these compounds, X is usually a detectable labeling group, which can, alternatively or in addition, serve as an affinity tag group (e.g. a glucose moiety) which can facilitate isolation of peptides modified with cysteine reactive agents; R is an amino acid reactive group capable of reacting with a cysteine residue at the sulfhydryl group or other location on cysteine; Y is usually a group that may optionally comprise a non-reactive functional group, or a functional group that can serve as, for example, a cross-linking moiety to effect cross-linking with other proteins, and/or as a detectable label, In the embodiment shown above, N is the nitrogen atom of an amide or amino functionality, and is covalently binds X, R and Y groups of the subject compounds.

The group X may comprise any labeling group or species that is detectable optically (including spectroscopically), radiometrically, magnetically, or by other detection technique as noted above. In the specific embodiments discussed herein, the group X comprises isotopic labeling groups that include one or more detectable isotopic labels of carbon, hydrogen, sulfur, fluorine, phosphorus, or other detectable radioactive labeling element used in the art. The labeling portion may in other embodiments comprise a fluorescent label that is spectroscopically detectable, or other form of labeling group.

The R group may comprise any functional group or moiety capable of reacting with a cysteine residue. In many embodiments, the R group is specifically reactive towards the sulfhydryl group of cysteine. The R group thus may comprise a reactive group capable of forming a carbon-sulfur bond, a sulfur-sulfur bond, or other covalent bond with a cysteine sulfhydryl group. In certain embodiments the sulfhydryl reactive portion may comprise a haloalkyl acyl group such as iodoacetamide, a maleimide a thiosulfonyl, or other sulfhydryl reactive group. In some embodiments, the R group is a a thiosulphonate group.

The Y group, in certain embodiments, may be a non-reactive functional group such as an alkyl, alkoxy, aryl, aryloxy or any other group that is stable or otherwise unreactive under conditions used for cysteine labeling and detection as described herein. In other embodiments the Y group may comprise a functional group that is specifically or non-specifically reactive towards other sites or functional groups present on proteins such that the subject compounds may serve as cross-linkers between the labeled or reacted cysteirie and another protein or another portion of the same protein. In this regard, the Y group may comprise a group that is specifically reactive for a hydroxyl group, free amino group, carboxylic group or other reactive functional group (other than a cysteine sulfhydryl group) present in a protein. In still other embodiments, the Y group may comprise an electron donating or electron drawing group that is conjugated to the R group and which serves to increase the reactivity of the R group to cysteine residues.

In certain embodiments, the Y group is a crosslinking moiety that covalently binds to amino acids. In these embodiments, the compound, therefore is a crosslinking compound that covalently links cysteine groups to other amino acids. In these embodiments, crosslinker compounds usually contain an affinity tag so that crosslinked peptides can be separated from excess uncrosslinked fragments. Crosslinker compounds usually have dimensions of about 1 Å to about 75 Å, about 10 Å to 50 Å or about 20 Å-40 Å, and capable of crosslinking a cysteine residue to another amino acid that is 1 Å to about 30 Å, about 3 Å to about 20 Å, about 5 Å to about 10 Å or about 6 Å away from the cysteine residue. Crosslinking compounds should also be soluble in water and suitable for use in a mass spectrometer. In certain embodiments, the crosslinking compounds may be cleavable in a mass spectrometer. Suitable crosslinking moieties include azide moieties, such as perfluoroaryazide, and active esters.

In another aspect, the invention features a kit comprising a composition described above, which composition is useful as a sulfhydryl-reactive agent. The kit can further comprise instructions for modification of a cysteine residue of a protein using the composition.

In one specific aspect, the method for analysis of protein structure according to the invention comprises producing a modified protein by coexpression of a polynucleotide encoding a mutant tRNA synthetase for misincorporation of a cysteine residue, and a polynucleotide encoding a protein of interest, wherein the coexpression results in production of a modified protein having a misincorporated cysteine residue (a "cysteine-modified" protein). After folding of the cysteine modified protein, it is contacted with a sulfhydryl-reactive compound under conditions suitable for modification of solvent accessible cysteine residues in the modified protein. Reaction of the sulfhydryl-reactive compound with the misincorporated cysteine residue indicates that the residue is solvent accessible. Detection of modification of cysteines can be accomplished by, for example, use of a reagent that cleaves unmodified, but not modified cysteines.

In a preferred embodiment, the sulfhydryl-reactive compound is an alkylating agent, such as iodoacetamide or a cysteine labeling reagent (hereinafter CLR). In some embodiments, the polynucleotide sequence encoding the protein of interest is modified prior to coexpression to remove or replace native cysteine residues in the protein.

In certain embodiments, the method of the invention further comprises use of two CLRs. For example, after contacting the modified protein with a first CLR having a 12C isotope label, the modified protein is contacted with a second CLR comprising the corresponding 13C isotope label. The ratio of 13C:12C reacted misincorporated cysteines, which can be determined by, for example, mass spectrometry, provides a measure of the relative accessibility of the misincorporated cysteine in the modified protein. Alternatively, the first CLR can be 13C-labeled and the second CLR can be 12C-labeled.

In one aspect, the invention features a method to determine macromolecular structures comprising utilizing cysteine labeling reagents (CLRs) developed by the inventors. The use of a CLR of the present invention in conjunction with an automated mass-spectrometry readout expands the MPAX method to a high-throughput format, which facilitates its application on a genomic scale.

The invention thus provides methods and compounds for probing the conformation and structure of large protein complexes, membrane proteins and other insoluble or partially folded polypeptides.

The invention also provides compounds which enable a more efficient protein footprinting analysis.

The invention also provides a high throughput method for protein studying protein structure.

The invention further provides a method for the rapid determination of ligand binding sites in proteins.

The invention further provides a method for de novo determinatin of protein three dimensional structure.

One advantage of the present invention is that the (MPAX) protein footprinting method overcomes many of the limitations of traditional protein footprinting by allowing for use of multiple probes in a single molecule, non-uniform cleavage methods, and lack of data at single amino acid resolution.

Another advantage of the present invention is that the MPAX method overcomes many of the limitations as to, for example, protein size, solubility, and the requirement for expensive, specialized equipment, which are often required in traditional structure determination methods such as X-ray crystallography and nuclear magnetic resonance.

Another advantage of the invention is that cysteine residues can be misincorporated at specific amino acid types at different positions within the amino acid sequence. The misincorporation efficiency at each amino acid type can be adjusted using genetic selection to select for mutant misincorporator plasmids.

Another advantage is the method of the invention requires only microgram quantities of material, is not limited by protein size, and, as such, is ideally suited to proteome-wide structural studies.

These and other advantages, and features of the invention will become apparent to those persons skilled in the art upon reading the details of the method of protein analysis as more fully described below.

BRIEF DESCRIPTION OF THE DRAWINGS

FIG. 1, panel A shows a cysteine tRNA with the valine anti-codon GAC competing with native valine tRNAs in the cell. FIG. 1, panel B shows misincorporated cysteines used as probes of solvent accessibility. FIG. 1, panel C depicts how changes in cysteine exposure that result from local protein unfolding or a conformational change can also be detected.

FIG. 3, panel A is an autoradiograph of an electrophoretic gel which shows that the yeast trisosephosphate isomerase (TIM) protein was expressed in the presence of the indicated misincorporator tRNA (Ile, Val or Lue), labeled at its C-terminus with radioactive phosphate, and cleaved at cysteine residues by treatment with 2-nitro-5-thiocyanobenzoic acid (NTCB).

FIG. 3, panel B is an autoradiograph of an electrophoretic gel which shows the fragments formed by NTCB cleavage of TIM with cysteine misincorporated at valine positions when treated with 10 mM iodoacetamide (IA) for two minutes in the presence or absence of 4 M guanidinium chloride (GdmCl).

FIG. 4, panel A is an autoradiograph of an electrophoretic gel showing the NTCB fragment pattern of the TIM protein after treatment with 10 mM iodoacetamide (IA) for two minutes in the presence or absence of 50 mM glyceraldehyde-3-phosphate (GAP), a TIM substrate.

FIG. 4, panel B is an illustration of the yeast TIM crystal structure showing the locations of amino acids protected from alkylation by the substrate, glyceraldehyde-3-phosphate.

FIG. 6, panel A is a graph of representative data showing the fractional cleavage at three valine positions (substituted by cysteine) with respect to alkylation time.

FIG. 6, panel B is a graph of the protection factor at each misincorporation site plotted against the fractional burial of the corresponding wild-type residue in the TIM crystal structure. Data are shown for isoleucine (closed circle), valine (closed triangle), and leucine (closed square) positions.

FIG. 6, panel C is an illustration showing the the crystal structure of yeast TIM. Residues with a protection factor less than 100 are generally near the surface of the protein, while residues with protection factors greater than 100 are generally in the interior of the protein.

FIG. 6, panel D is a graph of the unfolding free energy at valine 91 [calculated as RT*ln(protection factor)] plotted as a function of GdmCl concentration. The solid line is a linear fit of the data extrapolated to zero denaturant.

FIG. 8, panel A is a schematic overview of the mass spectrometry readout method of the invention.

FIG. 8, panels B and C are a mass spectrum and mass chromatogram, respectively, of a control experiment of a 1:1 mixture of 12C-CLR and 13C-CLR modified TIM peptide 139-145 [TLDVVER] containing cysteine misincorporated at L140.

FIG. 8, panels D and E are a mass spectrum and mass chormatogram, respectively, of the modified TIM peptide 139-145 [TLDVVER] prepared according to the scheme in FIG. 7, panel A with τ=10 minutes.

FIG. 8, panel F is a plot of the protection factors measured by mass spectrometry readout versus those measured by gel readout in accordance with the invention.

Figure 1:
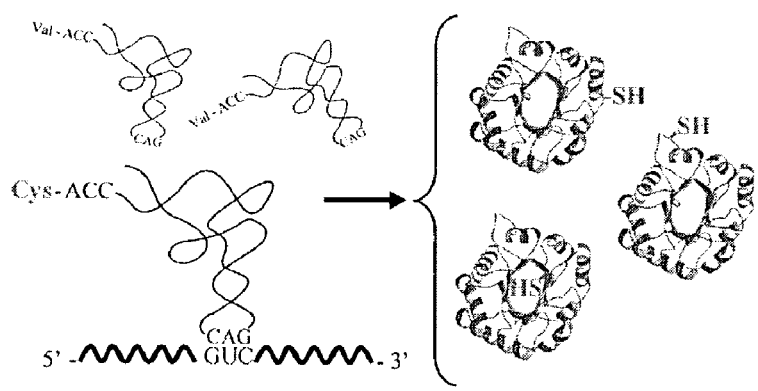
FIG. 1, panels A-C provide a schematic of the misincorporation proton-alkyl exchange (MPAX) method of the invention.
Figure 1:
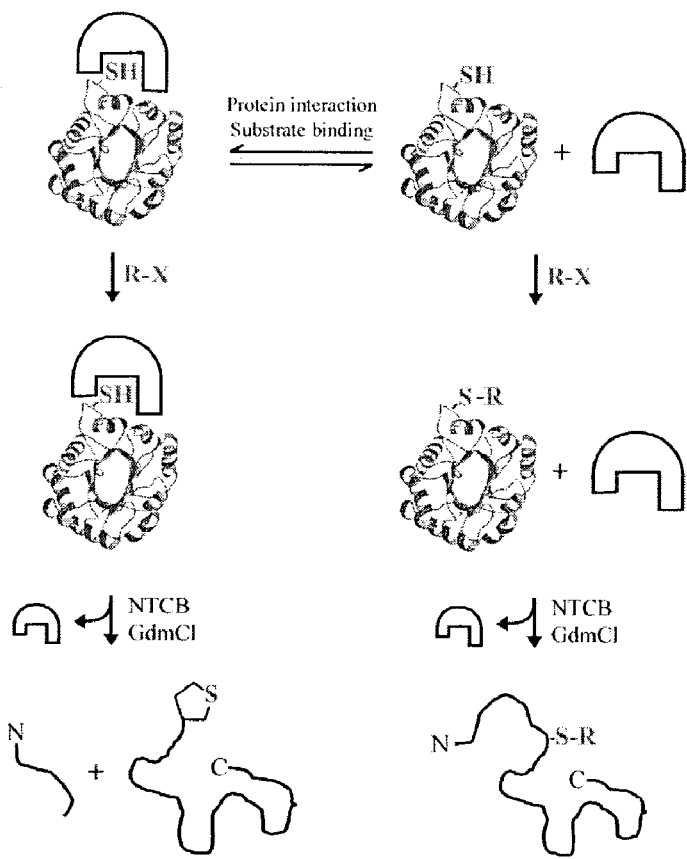
Figure 1:
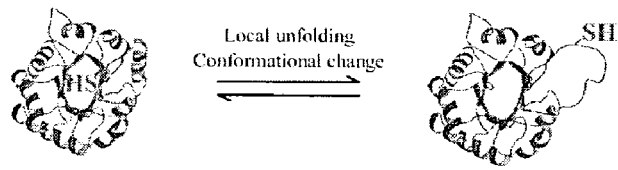

Models for the structures of I1 and I2 are shown. The native dimer (N) and the unfolded state (U) are also illustrated. Positions calculated to be more than 30% exposed to solvent in an intermediate structure are shaded a darker version of their original color.

Before the present invention is described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein, the singular forms "a", "and", and "the" include plural referents unless the context clearly dictates otherwise. Thus, for example, reference to "a protein fragment" includes a plurality of such fragments and reference to "the protein" includes reference to one or more proteins and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "protein footprinting" means the analysis of a protein's structure by measuring the solvent accessibility of regions of the amino-acid sequence to various modifying or cleavage reagents, including changes in accessibility due to the modulation of environmental factors. The term also means the analysis of a protein's structure by measuring amino acid proximity using crosslinking.

The term "cysteine labeling reagent (CLR)" means a cysteine-reactive molecule that can facilitate specific detectable labeling of cysteine residues and/or attachment of a moiety to facilitate isolation and separation of CLR-modified polypeptides. Generally CLRs are useful in protein analysis according to the methods described herein. Detectable labels of CLRs may be isotopic-based labels, fluorimetric labels, or other detectable molecular tags or labels. Affinity tags of CLRs can be any moiety that binds to a capture reagent to facilitate separation of CLR-modified polypeptides from non-CLR-containing materials in a sample.

"Cysteine-reactive", "sulfhydryl-reactive" and "thiol-reactive" is used herein to refer to an entity that reacts with an -SH group, such as present in a cysteine residue, which reaction is preferably specific (e.g., does not react with other amino acid moieties or side chains to a significant degree).

The term "MPAX" refers to the misincorporation proton-alkyl exchange method of protein footprinting as described herein.

The term "MXLINK" refers to the misincorporation crosslinking method of protein structure determination as described herein.

The term "MSX" refers to the misincorporation thiosulphonation method of protein footprinting, as described herein.

The term "yMPAX" refers to a misincorporation proton-alkyl exchange method of protein footprinting that is performed using cysteine-modified proteins made in *Saccharomyces cerevisiae*.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "cysteine modified protein" or "cysteine-misincorporated protein" refers to a protein of interest having at least one non-native cysteine residue.

The term "host cell" includes an individual cell or cell culture which can be or has been a recipient of any recombinant vector(s) or isolated polynucleotide of the invention.

Host cells include progeny of a single host cell, and the progeny may not necessarily be completely identical (in morphology or in total DNA complement) to the original parent cell due to natural, accidental, or deliberate mutation and/or change. A host cell includes cells transformed, transfected, or infected in vivo or in vitro with a recombinant vector or a polynucleotide of the invention. A host cell which comprises a recombinant vector of the invention is a "recombinant host cell."

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

"Alkyl" means a linear saturated monovalent hydrocarbon of one to six carbon atoms or a branched saturated monovalent hydrocarbon of three to six carbon atoms (e.g., methyl, ethyl, propyl, 2-propyl, butyl, pentyl, and the like), and further can be substituted by cycloalkyl groups.

"Cycloalkyl" means a cyclic saturated monovalent hydrocarbon group of three to seven carbon atoms, e.g., cyclopropyl, cyclohexyl, and the like.

"Alkenyl" means a linear monovalent hydrocarbon group of two to six carbon atoms or a branched monovalent hydrocarbon radical of three to six carbon atoms containing at least one double bond, e.g., ethenyl, 2-propenyl, and the like.

"Alkynyl" means a linear monovalent hydrocarbon group of two to six carbon atoms or a branched monovalent hydrocarbon radical of three to six carbon atoms containing at least one triple bond, e.g., ethynyl, propynyl, butynyl, and the like.

"Halo" means fluoro, chloro, bromo, iodo, and the like.

"Haloalkyl" means alkyl substituted with one or more halogen atoms, including those substituted with different halogens, e.g., —CH2Cl, —CF3, —CH2CF3, —CF2CF3, —CH2CCl3, and the like.

"Alkoxy", "alkenyloxy", "cycloalkyloxy", or "haloalkyloxy" refers to an —OR containing moiety where R is alkyl, alkenyl, cycloalkyl, or haloalkyl respectively as defined above, e.g., methoxy, ethoxy, propoxy, 2-propoxy, ethenyloxy, cyclopropyloxy, cyclobutyloxy, —OCH2Cl, —OCF3, and the like.

"Alkylthio" or "cycloalkylthio" refers to an —SR containing moiety where R is alkyl or cycloalkyl respectively as defined above, e.g., methylthio, butylthio, cyclopropylthio, and the like.

"Acyl" refers to a —C(O)R containing moiety where R is hydrogen, alkyl, or haloalkyl as defined above, e.g., formyl, acetyl, trifluoroacetyl, butanoyl, and the like.

"Amino" refers to an —NH2 containing moiety, (1-methylethyl)amino, and the like, including di-and tri-substituted aminos.

"Azide" means any compound containing the ion $N_3^-$ or the group —$N_3$

"Disubstituted amino" refers to a —NRR' containing moiety where R and R' are independently alkyl or acyl, e.g., dimethylamino, methylethylamino, di(1-ethylethyl)amino, and the like.

"Hydroxyalkyl" means a linear monovalent hydrocarbon group of two to six carbon atoms or a branched monovalent hydrocarbon group of three to six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4dihydroxybutyl and 2-(hydroxymethyl)-3-hydroxypropyl, 2-hydroxyethyl, 2,3-dihydroxypropyl, and 1-(hydroxymethyl)-2-hydroxyethyl.

"Alkoxyalkyl" means a linear monovalent hydrocarbon group of one to six carbon atoms or a branched monovalent hydrocarbon group of three to six carbons substituted with at least one alkoxy group as defined above, e.g., 2-methoxyethyl, 2-methoxypropyl, and the like.

"Hydroxyalkyloxy" or "alkoxyalkyloxy" means a group containing an —OR moiety where R is hydroxyalkyl or alkoxyalkyl respectively as defined above, e.g., 2-hydroxyethyloxy, 2-methoxyethyloxy, and the like.

"Aminoalkyl" means a linear monovalent hydrocarbon group of two to six carbon atoms or a branched monovalent hydrocarbon radical of three to six carbons substituted with at least one —NRR' where R and R' are independently selected from hydrogen, alkyl, or acyl, e.g., 2-aminoethyl, 2-N,N-diethylaminopropyl, 2-N-acetylaminoethyl, and the like.

"Aryl" means a monovalent monocyclic or bicyclic aromatic hydrocarbon group of 6 to 12 ring atoms, and optionally substituted independently with one or more substituents selected from alkyl, haloalkyl, cycloalkyl, alkoxy, alkylthio, halo, nitro, acyl, cyano, amino, monosubstituted,amino, disubstituted amino, -hydroxy, carboxy, or alkoxycarbonyl. Representative examples include, but are not limited to, phenyl, biphenyl, 1-naphthyl, and 2-naphthyl and the derivatives thereof.

"Heteroaryl" means a monovalent monocyclic or bicyclic aromatic group of 5 to 10 ring atoms containing one or more, sometimes one or two ring heteroatoms selected from N, O, or S, the remaining ring atoms being C. The heteroaryl ring is optionally substituted independently with one or more substituents, sometimes one or two substituents, selected from alkyl, haloalkyl, cycloalkyl, alkoxy, alkylthio, halo, nitro, acyl, cyano, amino, monosubstituted amino, disubstituted amino, hydroxy, carboxy, or alkoxycarbonyl. Specifically the term heteroaryl includes, but is not limited to, pyridyl, pyrrolyl, thienyl, furanyl, indolyl, quinolyl, benzopyranyl, and thiazolyl, and the derivatives thereof.

"Heterocycloamino" means a saturated monovalent cyclic group of 3 to 8 ring atoms, wherein at least one ring atom is N and optionally contains a second ring heteroatom selected from the group consisting of N, O, or $S(O)_n$ (where n is an integer from 0 to 2), the remaining ring atoms being C. The heterocycloamino ring may be optionally fused to a benzene ring or it may be optionally substituted independently with one or more substituents, sometimes one or two substituents, selected from alkyl, haloalkyl, cycloalkyl, cycloalkylalkyl, aryl, aralkyl, heteroaryl, heteroaralkyl, halo, cyano, acyl, amino, monosubstituted amino, disubstituted amino, carboxy, or alkoxycarbonyl. More specifically the term heterocycloamino includes, but is not limited to, pyrrolidino, piperidino, morpholino, piperazino, indolino, and thiomorpholino, and the derivatives thereof.

"Heterocyclo" means a saturated monovalent cyclic group of 3 to 8 ring atoms in which one or two ring atoms are heteroatoms selected from N, O, or $S(O)_n$, where n is an integer from 0 to 2, the remaining ring atoms being C. The heterocyclo ring may be optionally fused to a benzene ring or it may be optionally substituted independently with one or more substituents, sometimes one or two substituents, selected from alkyl, haloalkyl, cycloalkyl, cycloalkylalkyl, aryl, aralkyl, heteroaralkyl, halo, cyano, acyl, monosubstituted amino, disubstituted amino, carboxy, or alkoxycarbonyl. More specifically the term heterocyclo includes, but is not limited to, pyrrolidino, piperidino, morpholino, piperazino, tetrahydropyranyl, and thiomorpholino, and the derivatives thereof.

"Cycloalkylalkyl" means a group containing a —$R^aR^b$ moiety, where $R^a$ is an alkylene group and $R^b$ is a cycloalkyl group as defined above e.g., cyclopropylmethyl, cyclohexylpropyl, 3-cyclohexyl-2-methylpropyl, and the like.

"Cycloalkylalkyloxy" means a group containing an —OR moiety, where R is a cycloalkylalkyl group as defined above e.g., cyclopropylmethyloxy, 3-cyclohexylpropyloxy, and the like.

"Aralkyl" means a group containing a —RaRb moiety, where Ra is an alkylene group and R b is an aryl group as defined above e.g., benzyl, phenylethyl, 3-(3-chlorophenyl)-2-methylpentyl, and the like.

"Heteroaralkyl" means a group containing a —RaRb moiety, where Ra is an alkylene group and R b is a heteroaryl group as defined above e.g., 2-,3-, or 4-pyridylmethyl, furan-2-ylmethyl and the like.

"Heterocycloalkyl" means a group containing a —RaRb moiety, where Ra is an alkylene group and R b is a heterocyclo group as defined above e.g., morpholin-4-ylethyl, tetrahydrofuran-2-ylmethyl and the like.

"Optional" or "optionally" means that the subsequently described event or circumstance may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

DETAILED DESCRIPTION OF THE INVENTION

Overview

The invention is based on the discovery that controlled misincorporation of cysteine residues for selected amino acid residues in a protein can be used to provide probes for protein structure analysis.

Many embodiments of the invention include at least one of the three general aspects: 1) translational misincorporation to effect misincorporation of cysteine for a selected amino acid residue to produce an ensemble of "cysteine-modified" or "cysteine-misincorporated" proteins, which proteins comprise at least one non-native cysteine residue that serves as a "probe" for structural analysis; 2) analysis of the folded cysteine-misincorporated protein through protein footprinting, which involves chemical modification of the introduced cysteine side chain (e.g., thiol group) which can be by, for example, alkylation or other chemical modification; and 3) analysis of the structure of the chemically-modified, cysteine-misincorporated protein, which, in some embodiments, can be accomplished using CLRs using, for example, crosslinking CLRs. In general, the misincorporated cysteines serve as structural probes which are susceptible to chemical modification. In one embodiment, the application of the chemical cleavage at misincorporated cysteine residues as a readout of alkylation, and providing inexpensive reagents for mass labeling at cysteine residues.

In most embodiments of the invention, a single cysteine residue is misincorporated into a single protein molecule at a position corresponding to a particular amino acid, e.g. lysine, phenylalanine, etc. However, since that amino acid may be present at several positions in the protein, when a population of proteins is produced using the subject methods, cysteine residues may be incorporated at several different positions in the protein. As such, a population of proteins made from, e.g., bacteria or yeast, using the subject methods, may contain misincorporated cysteines at many different position corresponding to the chosen modified tRNA, each cysteine modified protein of the population usually contains one misincorporated cysteine.

In related embodiments, methods involving very rapid chemical modification of an introduced cysteine side chain using thiosulfonate reagents, and methods for producing cysteine-modified in yeast are discussed.

In alternative embodiments, as described above, cysteine modified proteins are produced, and the folded cysteine-modified protein is crosslinked (either intramolecularly, or intermolecuary) using a crosslinking agent that covalently binds the introduced cysteine side chain through, e.g. alkylation, and also covalently binds a nearby amino acid. In general, the crosslinked protein is subjected to proteolytic cleavage, and the crosslinked peptide fragments are purified by an affinity group present on the crosslinking agent. The crosslinked peptide fragments are then analyzed by any suitable method, e.g. mass spectrometry to determine which two amino acids are crosslinked.

The invention can be used to, for example, identify a binding site of an endogenous or non-endogenous ligand or substrate, identify domains of a protein, detect protein-protein interactions, analyze protein topology and three-dimensional structure, analyze kinetics of protein conformational changes, analyze protein stability, and identify binding domains and structural interactions between macromolecules having a polypeptide component.

Methods

The subject methods of the invention utilizes the sulfhydryl groups of cysteine residues as reactive sites that can be modified specifically under native conditions. Because cysteine residues occur naturally at low frequency, auxiliary cysteines are introduced into a protein of interest to act as structural probes. In the present invention, this is accomplished by misincorporation of cysteines through modification of protein translational machinery. Specifically, anti-codon variants of the cysteine tRNA that substitute cysteine residues for other (non-cysteine) amino acids are engineered for use in the methods.

A selected cysteine misincorporator tRNA is co-expressed with a protein of interest in a host cell (e.g., recombinant cell) or in vitro translation system. The host cell is usually a bacterial or yeast host cell, particularly one that is readily manipulated using molecular genetic techniques such as bacteria (e.g., *Escherichia coli*) or yeast (e.g., *Saccharomyces*, particularly *S. cerevesiae*). The nucleic acid encoding the misincorporator tRNA can be present on a plasmid or in the host cell chromosomal DNA. The protein of interest can be encoded by an nucleic acid present in the host cell chromosome, or on a construct, and may be either endogenous or non-endogenous (e.g., recombinant), usually non-endogenous, to the host cell. Where the misincorporator tRNA and the protein of interest are encoded in an expression construct, they may be on the same or different constructs, may both be present on the same or different host chromosome, or may be on the host chromosome and as an extrachromosomal element (e.g., the misincorporator tRNA may be present on the host chromosome and the protein of interest encoded in an expression construct). Expression of the misincorporator tRNA with the protein of interest results in low-frequency misincorporation of a cysteine residue in lieu of the amino acid recognized by the anti-codon sequence of the misincorporator tRNA. The proteins produced by this method are referred to herein as modified proteins, cysteine misincorporated proteins or cysteine modified proteins, interchangeably and without limitation.

The cysteine modified proteins are exposed to a thiol-specific modifying reagent, allowing modification of accessible cysteine residues. In some embodiments, the difference in the observed rate of modification at each misincorporated cysteine relative to the intrinsic rate of modification of a free thiol provides a measurement of the misincorporated cysteine's solvent accessibility. Cysteine modification can be measured by any suitable method, such as analysis by mass spectrometry or by common peptide separation techniques such as gel electrophoresis of the peptides generated by proteolysis or chemical cleavage of the modified protein fragmentation.

One embodiment of the invention termed the MPAX method, is outlined schematically in FIG. 1, panels A-C. FIG. 1, panel A shows a cysteine tRNA with the valine anti-codon GAC competing with native valine tRNAs in the cell. In the example depicted in FIG. 1, panels A-C, cysteine is misincorporated in place of valine at a low level, resulting in an ensemble of proteins containing single cysteine substitutions. FIG. 1, panel B shows that misincorporated cysteines can be used as probes of solvent accessibility. Exposed cysteines on the protein surface react with an alkylating reagent R-X to generate an alkylated sulfhydryl group. These alkylated cysteines are not susceptible to backbone cleavage when exposed to the cysteine-specific cutting reagent 2-nitro-5-thiocyanobenzoic acid (NTCB). Cysteines protected from solvent by protein-protein interactions or ligand binding are not alkylated, and are susceptible to backbone cleavage when exposed to NTCB. Cleavage fragments can be visualized by any suitable method, e.g. gel electrophoresis. FIG. 1, panel C demonstrates that changes in cysteine exposure that result from local protein unfolding or a conformational change can also be detected.

Figure 14:
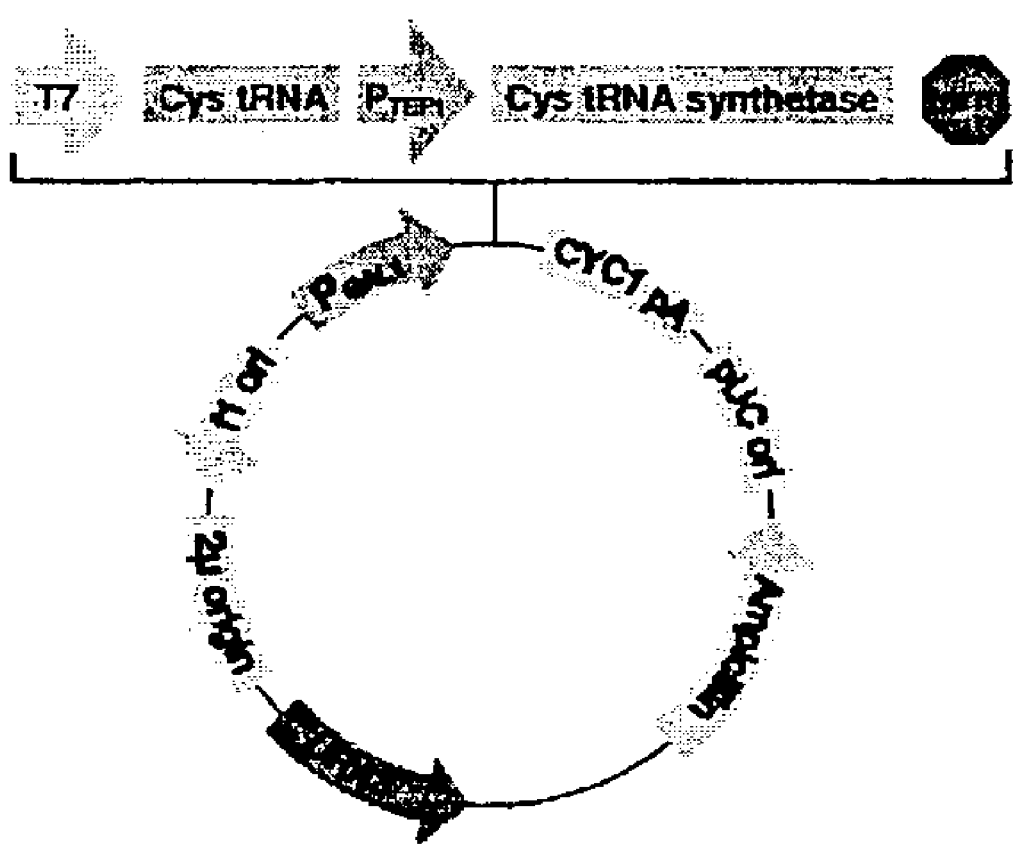
FIG. 14 is a schematic figure of a construct for use in yeast MPAX methods.

The MPAX technique of the invention can be used in mapping the binding sites for small molecules and protein ligands on a protein of interest, in both native and unfolded states. MPAX has many applications beyond those specifically enunciated here. For example, time-resolved measurements of cysteine reactivity can be used to monitor the kinetic progression of biochemical events. Alkylation of misincorporated cysteines in vivo can probe protein interactions in their natural environment. The ensemble of proteins containing misincorporated cysteines can be tested in a mutagenesis interference experiment to assess which cysteines interfere with functional properties of the protein. Functional and non-functional populations can be separated and the presence of misincorporated cysteines quantitated in each population by mass spectrometry or electrophoretic methods as described above. The MPAX method can also be adapted to eukaryotic expression systems known to accommodate suppressor tRNAs (F. A. Laski, F. A. et al., *Proc. Natl. Acad. Sci. U.S.A.* 86, 6696 (1989); Park, H. J., and U. L. RajBhandary, *Mol. Cell Biol.* 18, 4418 (1998)). A plasmid suitable for use in Saccharomyces cerevisiae is shown in FIG. 14.

In a method that is related to MPAX that is known as MSX, cysteine modification by e.g. thiosulfonate is performed. In these embodiments, the reaction of cysteine side change with thiosulfonates occurs with a second order constant of about $8 \times 10^{-5} M^{-1} s^{-1}$ at pH 9.0, and, as such, the half-life for disulfide bond formation is 87 microseconds at 10 mM thiosulfonate. Thiosulfonates may therefore used in a footprinting technique that can measure solvent accessibility in a protein over very short periods of time, such as milliseconds.

Figure 9:
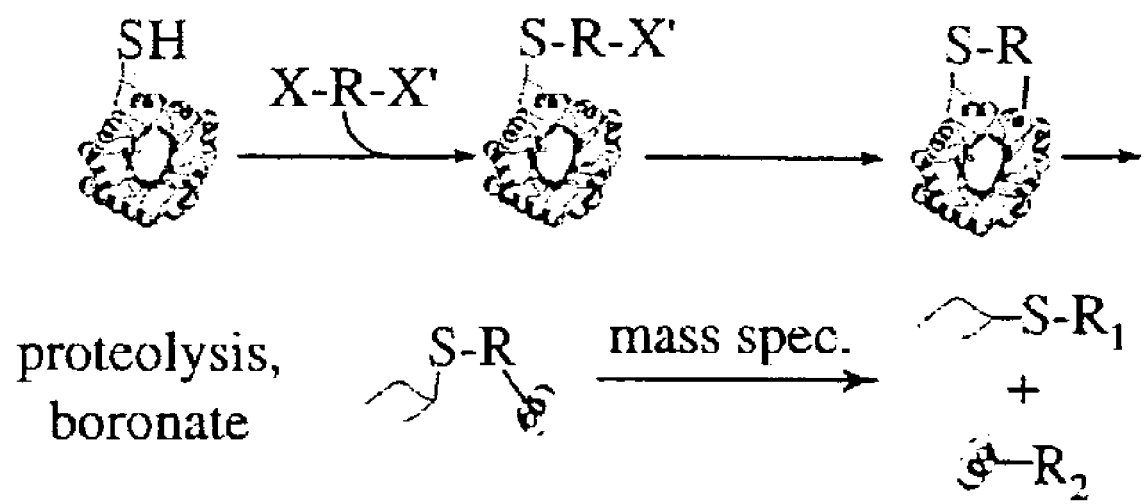
FIG. 9 is a schematic overview of the MXLINK method.

Cysteine-misincorporated proteins may also be used with crosslinking agents to determine pairwise amino acid proximity. These methods are termed MXLINK methods. MXLINK methods are schematically described in FIG. 9. Cysteine-misincorporated proteins are modified by a suitable crosslinking agent shown in FIG. 9 by the formula X—R—X', which corresponds to a CLR where Y is a crosslinker, as will be further described in greater detail below. FIG. 9 shows a crosslinking agent that covalently links to a cysteine side group. Following linkage to a cysteine, the agent is crosslinked to an adjacent or proximal amino acid (i.e. an amino acid that is about 1 Å to about 30 Å, about 3 Å to about 20 Å, about 5 Å to about 10 Å or about 6 Å from the cysteine) the crosslinked protein is subject to proteolysis, and the crosslinked peptide fragments purified by any suitable method. In the embodiment shown in FIG. 9, the fragments are purified by boronate, e.g. a phenylboronic acid resin, that binds to a glucose affinity tag on the crosslinker. Once purified, the crosslinked fragments are analyzed by mass spectrometry to determine the identity of the proximal amino acid and the cysteine-misincorporated amino acid. In certain embodiments, the crosslinked fragments are further fragmented and analyzed by MS/MS, yielding the amino acid linked to the crosslinker.

Once proximal amino acids are determined for a plurality of amino acid pairs for a protein, a three dimensional structure of at least part of the protein may be produced by determining the spatial relationships between the amino acids. In these embodiments, a plurality is at least about 10, at least about 20, at least about 50, at least about 100, at least about 200, at least about 300, at least about 500, at least about 1000, at least about 1500, at least about 2000, or at least about 5000 or more, usually up to about 1000.

Taken together, these approaches will make possible detailed structural investigations of complex, and formerly inaccessible, biological processes.

Various aspects of the subject methods are described in more detail below.

Misincorporation of Cysteine Residues

Misincorporation of cysteines can be generally accomplished by producing a misincorporator construct or plasmid which expresses a Cys tRNA and, present in many cases but not necessarily essential, a cysteinyl tRNA synthetase. In general, the misincorporator plasmid comprises a polynucleotide encoding a tRNA specific for cysteine ("Cys tRNA") operably linked to a promoter, and a polynucleotide encoding a cysteinyl tRNA synthetase and its operably linked promoter. The Cys tRNA and cysteinyl tRNA synthetase coding sequences can be operably linked to the same or different promoters. The promoters can be any suitable promoter selected according to the host cell, e.g., a promoter adapted for expression of a coding sequence in a bacterial host cell, such as a T7 promoter. The sequences of tRNA and tRNA synthetase polynucleotides useful in producing a misincorporator plasmid may be sequences derived from mammals, insects or bacteria (e.g. cysteine tRNA and cysteinyl tRNA synthetase polynucleotide sequences from *E. coli*) or other species where the cysteine tRNA and/or cysteinyl tRNA synthetase polynucleotide sequences are known and readily obtainable from such sources as Genbank. The constructs used in the invention can be any suitable replicable recombinant expression vehicle, including plasmids. Constructs vectors, and plasmids are used interchangeably herein and without limitation.

The derivative misincorporator plasmids can be generated by mutation of the tRNA anti-codon sequence using any site-specific mutagenesis protocol (for example, Kunkel mutagenesis (Kunkel, T. A., et. al., *Methods Enzymol.* 204: 125, 1991)). Libraries composed of various mutant cysteine tRNA-expressing constructs (referred to herein as pMPAX constructs) can be generated and transformed in appropriate cells to select mutant misincorporator plasmids with altered misincorporation efficiency. The library approach can thus generate new pMPAX constructs, with at least one construct being suitable for misincorporation of cysteine at each of the amino acid codons, as illustrated in the table below.

TABLE 1

| First nucleotide | Second nucleotide | | | | |
|---|---|---|---|---|---|
| | U | C | A | G | |
| U | UUU Phe | UCU Ser | UAU Tyr | UGU Cys | U |
| | UUC Phe | UCC Ser | UAC Tyr | UGC Cys | C |
| | UUA Leu | UCA Ser | UAA STOP | UGA STOP | A |
| | UUG Leu | UCG Ser | UAG STOP | UGG Trp | G |
| C | CUU Leu | CCU Pro | CAU His | CGU Arg | U |
| | CUC Leu | CCC Pro | CAC His | CGC Arg | C |
| | CUA Leu | CCA Pro | CAA Gln | CGA Arg | A |
| | CUG Leu | CCG Pro | CAG Gln | CGG Arg | G |
| A | AUU Ile | ACU Thr | AAU Asn | AGU Ser | U |
| | AUC Ile | ACC Thr | AAC Asn | AGC Ser | C |
| | AUA Ile | ACA Thr | AAA Lys | AGA Arg | A |
| | AUG Met | ACG Thr | AAG Lys | AGG Arg | G |
| G | GUU Val | GCU Ala | GAU Asp | GGU Gly | U |
| | GUC Val | GCC Ala | GAC Asp | GGC Gly | C |

TABLE 1-continued

| First nucleotide | Second nucleotide | | | | |
|---|---|---|---|---|---|
| | U | C | A | G | |
| | GUA Val | GCA Ala | GAA Glu | GGA Gly | A |
| | GUG Val | GCG Ala | GAG Glu | GGG Gly | G |

The codon used as the anti-codon on the tRNA can be selected according to the relative codon usage in the nucleic acid encoding protein of interest to be expressed. The efficiency of cysteine misincorporation associated with each pMPAX in a given host cell can be determined by co-transforming a host cell with a pMPAX constructs and a nucleic acid encoding a control protein coexpressing the constructs and analyzing the percentage of cysteine misincorporation in the control protein.

In some embodiments, multiple cysteine-inodified proteins based upon a protein of interest for structural analysis may be prepared with cysteine misincorporation for different amino acids. The fragmentation pattern of the various cysteine-modified proteins can then be analyzed, either individually or in parallel (e.g., on a single gel or gel lane) to identify and characterize multiple amino acid sites at one time. For example, cysteine-modified proteins include (with the amino acid to be replace by Cys listed first): Alanine (Ala)-Cys; Arginine (Arg))-Cys; Aspartic Acid (Asp)-Cys; Asparagine (Asn)-Cys; Glutamic Acid (Glu)-Cys; Glutamine (Gln)-Cys; Glycine (Gly)-Cys; Histidine (His)-Cys; Isoleucine (Ile)-Cys; Leucine (Leu)-Cys; Lysine (Lys)-Cys; Methionine (Met)-Cys; Phenylalanine (Phe)-Cys; Proline (Pro)-Cys; Serine (Ser)-Cys; Threonine (Thr)-Cys; Tryptophan (Trp)-Cys; Tyrosine (Tyr)-Cys; and Valine (Val)-Cys.

Cysteine-modified proteins useful in the invention comprise at least one non-native cysteine in lieu of a non-cysteine amino acid residue. While it is preferred that the modified protein contain a single non-native cysteine, the invention also contemplates modified proteins having two or more, three or more, four or more, five or more, up to ten or more non-native cysteines, which non-native cysteines may be present in lieu of the same native amino acid residue or different amino acid residues.

For example, in some embodiments, it is useful to utilize a plurality of different misincorporator tRNAs in one sample allowing analysis of a protein by modification of two, and in some instances three or more, different amino acids at one time. When the amino acid to be misincorporated by cysteine appears in the protein sequence only once or a few times, the proteomic analysis of the protein may be expedited by misincorporating cysteine for two or more types of amino acids. Because of the natural variation in codon usage within an organism, it is also useful to combine misincorporator tRNAs specific to different codons of the same amino acid Proteins of Interest to be Modified by Cysteine Misincorporalion The protein of interest for analysis can be any of a variety of proteins including, but not necessarily limited to, receptors, ligands (e.g., which can be analyzed to determine which residues of a ligand and a receptor interact, to examine the effect of ligand binding upon protein conformation, and the like), protein binding partners, and the like. The method of the invention finds particular utility in its application to membrane proteins, large protein complexes, and insoluble or disordered proteins for which no other methods can be efficiently applied to their study. The method will also be useful in the study of conformational changes in proteins, and in measuring the quantitative energetic stability of protein structures and subdomains, especially in proteins which do not exhibit reversible unfolding in bulk measurements.

The expression construct for the protein of interest generally comprises a polynucleotide encoding a protein of interest, which polynucleotide is operably linked to a promoter adapted for expression in a recombinant host cell. In certain embodiments the polynucleotide of interest is amplified by PCR, adding a protein kinase A tag or other protein tag labeling or affinity purification tag and cloned into a construct for expression according to methods well known in the art. Constructs, plasmids, and vectors are used herein to refer to nucleic acid molecules that are suitable for expression of a protein of interest, and are used interchangeably and without limitation. Constructs useful in the invention include any of a variety of commercially available constructs. The plasmid pET28a (Novagen, Madison, Wis.) is of particular interest.

As noted above, exemplary host cells suitable for use in the invention include any cell commonly utilized for prokaryotic or eukaryotic expression systems, and for which misincorporator constructs can be readily produced (e.g., *E. coli, Saccharomyces cerevisiae*, with *E. coli* being of particular interest). In vitro translation systems containing either expressed or exogenous tRNAs are also suitable for use. Exemplary misincorporator constructs useful in the invention are described in the Examples below (see, e.g., TABLE 2, which provides exemplary constructs developed for use in *E. coli*). Further expression systems include insect, and mammalian cell expression systems such as Drosophila Sf9 cells, baculovirus expression systems, and CHO cells, as is known in the art (e.g., Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.).

The protein of interest, once expressed by the expression system along with a misincorporator tRNA, is isolated and purified in a manner similar to how the native protein without misincorporation would be purified. The isolated protein is then folded. Methods for protein folding are selected according to the protein to be analyzed, and as such will vary.

Modification of Solvent Accessible Misincorporated Residues with a Reactive Compound.

Modification of cysteines generally involves chemical modification of the folded protein using a modifying agent, usually a sulhydryl-reactive agent, that preferentially specifically reacts with the thiol group of cysteine residues. The modifying agent is generally suspended in the solvent, which can penetrate the folded cysteine-modified protein to varying degrees, so that cysteines on or relatively closer to the surface of the folded protein are modified more readily than cysteines that are "buried" or relatively further from the surface of the folded protein.

In one embodiment of particular interest, chemical modification of cysteines is accomplished by alkylation of accessible cysteine residues with an alkylating agent. A "parent", unmodified folded protein can be subjected to chemical modification as a comparative control. Further, the folded protein(s) can be, subjected to chemical modification for varying amounts of time, thus providing for analysis of the rate at which the cysteine is modified. The rate of modification in the folded protein provides information on the degree of burial of the cysteine residue and the energetic stability of the unfolding subdomain in which the cysteine is located. The proteins can also be subjected to chemical modification under various conditions such as in the presence or absence of a substrate or ligand (e.g., proposed or known endogenous substrate or ligand), the presence or absence of an inhibitory compound or candidate drug or agent, and the like to assess the region of the protein that is in contact with such substrates, ligands, compounds, agents, and the like.

Modifying agents useful for the MPAX method of the invention include any agent that specifically forms a covalent bond with a cysteine residue. Exemplary modifying agents include, but are not necessarily limited to, iodoacetamide, a cysteine labeling reagent (CLR) described herein, N-ethylmaleimide (NEM), maleimido-dioxaoctylamine (MADOO), N-methyl-maleimide (NMM), iodoacetic acid, methylmethane-thiolsulfonate (MMTS), dithionitrobenzoic acid (DTNB), and the like. In order to facilitate the detection of modified cysteine residues, the modifying agents may be radioactively labeled, isotopically enriched, comprise a fluorophore component and/or an affinity tag component.

In one embodiment, iodoacetamide is reacted with the accessible cysteines of the folded cysteine-modified protein. Multiple samples may be prepared in which the duration of the alkylation reaction is varied to determine the rate of alkylation of cysteines within the folded protein. In one embodiment, the protein is reacted with a first alkylating agent having a first detectable moiety and, preferably following a step to remove unreacted first agent, reacted under denaturing conditions with a second alkylating agent having a second detectable moiety, where the first and second detectable moieties are different, and can be distinguished one from another. The ratio of first and second agents at each modified cysteine position reports on the extent of reaction of the cysteine side chain during the first agent incubation relative to the total possible extent of reaction.

In other embodiments, the accessible cysteines in the protein are alkylated with a cysteine labeling reagent (CLR) described herein. In one embodiment, the protein is first reacted with a first CLR having a first carbon isotope (e.g., $C^{12}$ or $C^{13}$) and, preferably following a step for removal of unreacted first CLR, reacted with a second CLR having a different, second carbon isotope. The protein of interest can then be fragmented by either chemical or enzymatic cleavage, the modified peptide fragments purified from unmodified peptides (e.g., using affinity purification, such as boronate affinity purification), and the peptide fragments analyzed by mass spectrometry.

The rate of modification (e.g., alkylation) of cysteine residues can be determined with any of the above agents by varying the duration of the reaction and comparing the relative levels of modification of specific cysteine residues versus time. Determining the rate of alkylation facilitates determining protection factors for each cysteine in the protein of interest. Pulse-chase experiments utilizing the CLRs of the invention also allow for the determination of protection factors for the misincorporated cysteine residues. Protection factors measure the amount of protection a misincorporated cysteine has from the modifying agent due to the protein structure. Large protection factors indicate cysteine side-chain burial in the native protein structure or burial caused by the binding of a substrate or ligand.

Because typical cysteine misincorporation frequencies in the present invention are, for example, about 1% per site a very small fraction of protein molecules expressed in the host cell are expected to contain more than a single cysteine substitution. One percent misincorporation means that at every amino acid position where misincorporation can occur, about 1% of the protein molecules expressed in the host cell will contain a cysteine at that location. Since the misincorporation sites are independent, the more misincorporation sites there are in the protein, the higher the expected chance of finding more than one cysteine in a given protein molecule. Rates of modification at slowly reacting sites can be measured accurately despite the existence of rapidly reacting sites, since the misincorporated cysteines are located in different molecules. The method is not limited by protein size or solubility and requires only microgram quantities of material.

In other embodiments, the proteins are contacted with two different modifying agents and under two different conformational states. For example, the accessible cysteines of the protein in one state (e.g. natively folded, in the presence of a ligand, and the like) may be alkylated with a modifying reagent enriched in one isotope, followed by placing the protein in a new state (e.g. denatured, in the absence of a ligand, etc.) and alkylating the accessible cysteine residues not already alkylated. The alkylation reactions are followed by either chemical (e.g. CNBr, cleavage of peptide bonds adjacent to Met) or enzymatic (e.g. trypsin (cleavage of peptide bonds adjacent to Lys and Arg), chymotrpysin, etc.) cleavage of the protein of interest.

Of particular interest is the modification of cysteine residues using a CLR of the invention, which reagents are described below in more detail. The use of the CLRs of the invention allows for purification of the peptide fragments modified by a CLR on a boronate column due to the presence of the diol group(s) on the CLR.

Analysis of Solvent Accessibility of Misincorporated Residues

Positional determination of modified cysteine residues, e.g., non-native cysteine residues introduced into the protein by misincorporation can involve proteolysis of the chemically modified (e.g., alkylated) protein (e.g., by chemical or enzymatic cleavage) and analysis of the peptide fragment pattern. The protein can be retained in folded conformation, or denatured prior to chemical modification. Preferably the chemically modified protein is denatured to allow access for cleavage of non-chemically modified cysteine residues.

The peptide fragment pattern will vary according to the modification of the cysteines in the protein. For example, where modification results in inhibition of cleavage of the protein backbone at the chemically modified cysteine, proteolysis of a protein that contains more modified cysteine residues will result in production of fewer peptide fragments than the same protein that has fewer modified cysteine residues. Alternatively, a modifying reagent (eg. NTCB) may be used that promotes cleavage of the backbone, in which case the pattern is reversed. Peptide fragments produced by proteolysis of a chemically modified, cysteine-modified protein can be compared to cleavage of the same protein that was not chemically modified, to chemically modified, "parent" protein (without non-native cysteines), or both.

Methods and reagents for proteolysis of proteins are well known in the art. Chemical cleavage can be accomplished using, for example, CNBr, which facilitates cleavage of peptide bonds adjacent to Met. Enzymatic cleavage can be accomplished using, for example, trypsin (cleavage of peptide bonds adjacent to Lys and Arg), chymotrpysin, and the like. Preferable cleavage of the protein into fragments allows for distinction between fragments of proteins that differ in the number or extent of modified cysteine residues. The analysis of the protein fragments may be completed by separation techniques such as gel electrophoresis, liquid chromatography, mass spectrometry, and combinations thereof (e.g., liquid chromatography/mass spectrometry (LC/MS)).

In one embodiment, after chemical modification of the folded protein by alkylation, the protein is contacted with 2-nitro-5-thiocyanobenzoic acid (NTCB) under denaturing conditions to react with the thiols of cysteines which were not alkylated. The alkylated cysteines are protected from backbone cleavage by NTCB, a cysteine-specific cutting compound (Jacobson G. R et. al., *J. Biol. Chem.* 248, 6583, 1973). A comparison of the peptide fragment pattern and band intensity of alkylated protein samples vs. unalkylated protein samples allows for the identification of misincorporated cysteines which are accessible to the alkylating agent.

Because misincorporation can be designed to occur at a single amino acid type (e.g., Ala substituted with Cys), as determined by the type of misincorporator tRNA utilized in the method, cleavage sites are generally distant in the sequence, and cleavage fragments can be separated using SDS-PAGE. Combining data from separate samples for misincorporation at different amino acids can thus provide structural infonnation at single amino acid resolution.

Of particular interest is the use of the CLRs of the invention, described below in more detail, for cysteine modification and analysis. As with the other embodiments of the method of the invention, the peptide fragments are analyzed to determine the solvent accessibility, protection factor and position of the misincorporated cysteine within the protein of interest. The preferable method of analysis when utilizing the CLR for alkylation is mass spectrometry.

Cysteine Labeling Reagents (CLRs)

The invention also provides CLRs. The subject CLRs have three functional groups, X, Y and R, which can be arranged in the CLR in any way (e.g. linearly, as branches from a backbone molecule, or joined to a linking molecule, such as a nitrogen, for example) to provide a CLR suitable for its intended purpose. One suitable CLR of the invention is be described by the generic formula:

where, X is usually a detectable labeling group, which can, alternatively or in addition, serve as an affinity tag group to facilitate isolation of proteins modified with cysteine reactive agents; R is an amino acid reactive group capable of reacting with a cysteine residue, preferably at the thiol or sulfhydryl group; Y is a group that may optionally comprise a non-reactive functional group, or a functional group that can serve as, for example, a cross-linking moiety to effect cross-linking with other proteins, and/or as a detectable label. In the embodiment shown above, N is the nitrogen atom of an amide or amino functionality, and covalently bonded to the X, R and Y groups of the subject compounds.

The group X may comprise any labeling group or species that is detectable optically (including spectroscopically), radiometrically, magnetically, or by other detection technique as noted above. In the specific embodiments discussed herein, the group X comprises isotopic labeling groups that include one or more detectable isotopic labels of carbon, hydrogen, sulfur, fluorine, phosphorus, or other detectable radioactive labeling element used in the art. The labeling portion may in other embodiments comprise a fluorescent label that is spectroscopically detectable, or other form of labeling group.

In some embodiments, X serves as a moiety that facilitates isolation of the CLR, particularly in the context of a CLR-modified cysteine residue in a polypeptide, which moieties are referred to herein as "affinity tags". Suitable affinity tags are those that selectively bind a capture reagent, either covalently or non-covalently, with an affinity and avidity sufficient to separate a CLR-modified polypeptide from non-CLR containing materials present in a sample (e.g., polypeptide not modified by CLR). Preferably, the affinity group-capture reagent interaction is reversible, so as to allow for separation of CLR-modified polypeptides from the capture reagent. Exemplary affinity tag-capture reagent pairs include: 1,2-diol groups (such as 1,2-dihydroxyethane and other 1,2 dihydroxyalkanes including those of cyclic alkanes, which bind to an alkyl or aryl boronic acid or boronic acid ester, such as phenyl $B(OH)_2$ or hexyl-B $(OEthyl)_2$, which may be immobilized on a support (as in a boronate resin); charged moieties and ion exchange resins, antigen-antibody pairs, including hapten-antibody pairs, such as in immunoaffinity separation columns; ligand-receptor pairs; and the like. In one embodiment, the affinity tag is a glucose moiety.

The R group may comprise any functional group or moiety capable of reacting with a cysteine residue. In many embodiments, the R group is specifically reactive towards the sulfhydryl group of cysteine. The R group thus may comprise a reactive group capable of forming a carbon-sulfur bond, a sulfur-sulfur bond, or other covalent bond with a cysteine sulfhydryl group. In certain embodiments the sulfhydryl reactive portion may comprise a haloalkyl acyl group such as iodoacetamide, a maleimide a thiosulfonyl, or other sulfhydryl reactive group.

The Y group, in certain embodiments, may be a non-reactive functional group such as an alkyl, alkoxy, aryl, aryloxy or any other group that is stable or otherwise unreactive under conditions used for cysteine labeling and detection as described herein. In other embodiments the Y group may comprise a functional group that is specifically or non-specifically reactive towards other sites or functional groups present on proteins such that the subject compounds may serve as cross-linkers between the labeled or reacted cysteine and another protein or another portion of the same protein. In this regard, the Y group may comprise a group that is specifically reactive for a hydroxyl group, free amino group, carboxylic group or other reactive functional group (other than a cysteine sulfhydryl group) present in a protein. In still other embodiments, the Y group may comprise an electron donating or electron withdrawing group which serves to increase the reactivity of the R group to cysteine residues.

In one embodiment of the CLR reagents of the invention, X is a 1,2 diol containing group which can be isotopically labeled. X is often derived from sugars, which naturally contain vicinal diol groups, while group Y, when present as a functional group, is generally derived from primary amines, although neither of these is required. The reactive group is generally introduced by acylation of the secondary amine produced by coupling of groups X and Y, although many strategies by which these molecules could be produced are well known in the art. In one embodiment, a CLR of the invention comprises an radioisotope-labeled moiety, a cysteine-reactive moiety capable of reacting with a free thiol of a cysteine residue in a peptide or protein. The isotope-labeled moiety may be derived from a variety of isotope labeled precursor molecules such as, for example, $^{13}C$-labeled and $^{12}C$-labeled glucose, glucamine, fructose or other 1,2 diol containing hydrocarbon chains. The cysteine-reactive moiety may comprise, for example, an iodoalkyl group such as an α-iodo carbonyl or α-iodo amide capable of forming a carbon-sulfur bond via nucleophilic displacement of the iodo group by a cysteine thiol. Other reactive groups such as maleimide or thiosulfonate derivatives are also possible.

Other embodiments of CLR molecules comprise further substitution of the amine group. One exemplary molecule incorporates a chlorine atom, whose characteristic natural isotope abundance allows identification of modified peptides by mass spectrometry. Another exemplary molecule incorporates a cross-linking or side-chain reactive group such as, for example, a 4-azidobenzyl group or other benzyl group with a reactive group that is capable of forming a covalent bond with one or more types of functional groups present in peptide or protein side chains. Yet another exemplary molecule incorporates a fluorescent moiety such as, for example, pyrene or fluorescein, which provides a means to visualize proteins with modified misincorporated cysteines.

In certain embodiments, the CLR is an isotope coded affinity tag of the following structure:

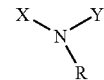

where R is a thiol reactive group, as described above, Y comprises an electron donating or electron withdrawing group which serves to increase the reactivity of the R group to cysteine residues, and X is an affinity tag, as described above. In certain embodiments, the CLR has the following structure:

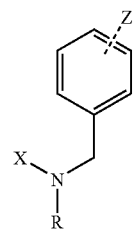

where Y is a halobenzyl group, and Z is a halide (e.g. F, I, Br etc). In other embodiments, the CLR contains a parahalobenzyl group and has the following structure:

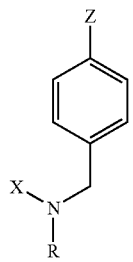

As will be described in greater detail below, the CLR X group may contain $^{12}C$, $^{13}C$ or $^{14}C$ atoms, in any combination.

Figure 2:
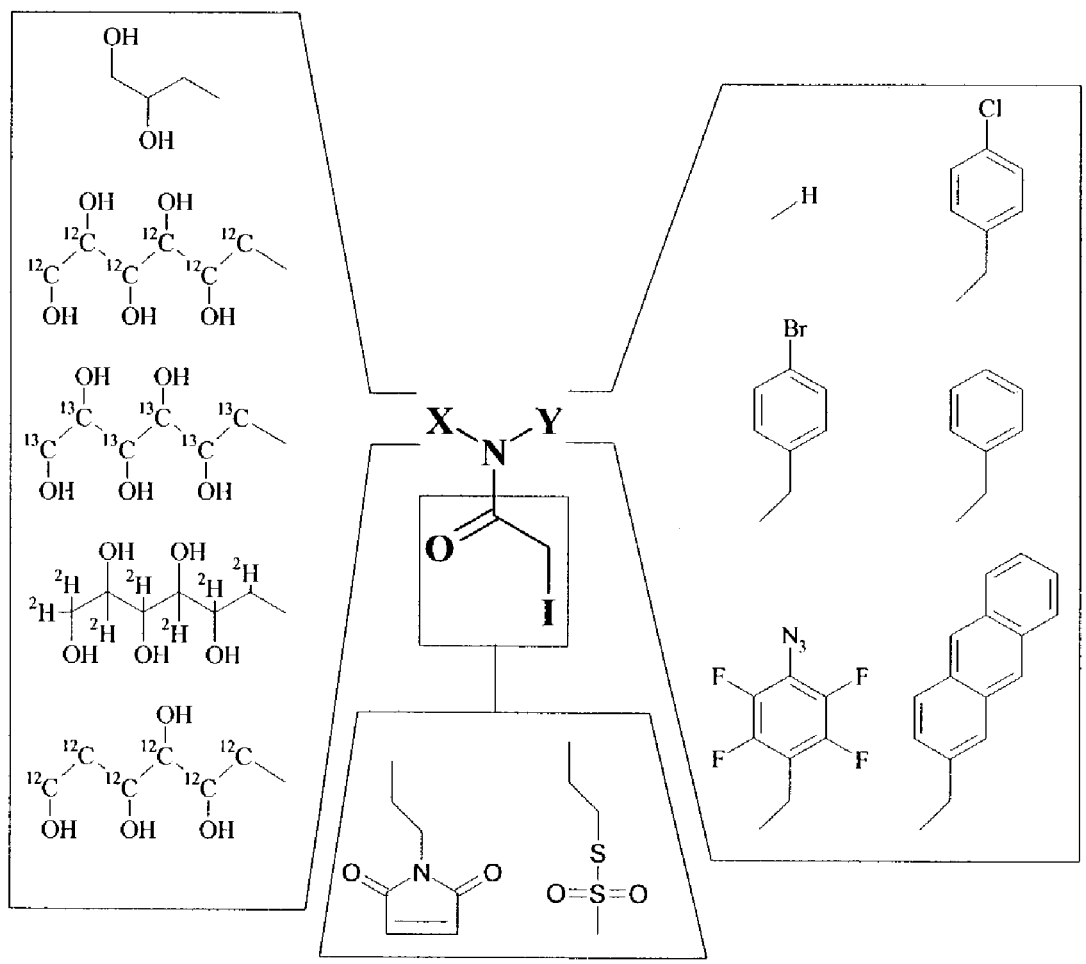
FIG. 2 is a schematic showing exemplary CLRs of the invention.

Exemplary CLRs of particular interest are illustrated in FIG. 2, where the exemplary groups illustrated in the positions of X, Y, and R can be provided in any combination. CLRs of particular interest, which are exemplified below as detectably and isotopically labeled, are illustrated below:

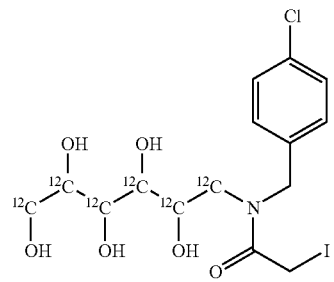

N-(iodoacetyl, p-chlorobenzyl)-glucamine

These specific molecules are referred to in the Examples below as $^{12}C$-CLR and $^{13}C$-CLR. Variations of CLRs described herein will be readily apparent to the ordinarily skilled artisan. For example, the group Y, exemplified above as a chlorine, can be any suitable halo group (e.g., Br or F), or other functionality that can, through electronic conjugation with the sulfhydryl-reactive group, increase the sulfhydryl-reactive group's reactivity with, or specificity for, cysteine residues.

In one embodiment, Y provides for cross-linking of a CLR-modified cysteine with another amino acid in the same polypeptide or in a different polypeptide (e.g., to provide an intramolecule or intermolecular cross-link, where an exemplary intermolecular cross-link may be between, for example, a polypeptide and its associated ligand). Preferably, where Y is a cross-linking moiety, Y is a nitrene-containing group. Where Y is a nitrene containing group, Y can be any nitrene-containing aryl or heteroaryl group. Where the nitrene group is preferably at the 4 (para) position, it may also be at the 2 or 6 (ortho) position, although the ortho positions are less preferred. The —$N_3$ group can be activated by UV light following modification of a cysteine residue with the protein-reactive group R. The nitrene group can react with a wide variety of sidechains, and results in covalent linkage of the CLR-modified cysteine to a nearby amino acid sidechain. The cross-linked polypeptides can then be isolated and analyzed.

An exemplary CLR having a cross-linking moiety is provided below:

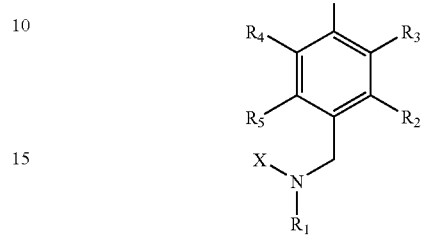

wherein, where $R_1$ is R, and $R_2$, $R_3$, $R^4$, and $R_5$ can be any suitable electron-withdrawing group, paticularly a halo group (e.g., F, Br, Cl, and the like) or a trifluoromethyl ($CF_3$) group. The groups at $R_2$, $R_3$, $R^4$, and $R_5$ can be the same or

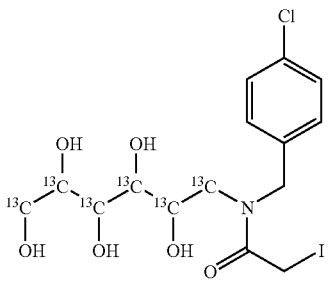

different, and preferably are the same. In one embodiment, each of $R_2$, $R_3$, $R_4$, and $R_5$ are halo groups, preferably fluorine.

An exemplary nitrene-containing CLR compound of particular interest is provided below.

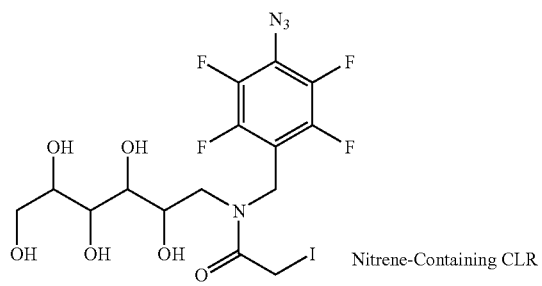

Nitrene-Containing CLR

Figure 10:
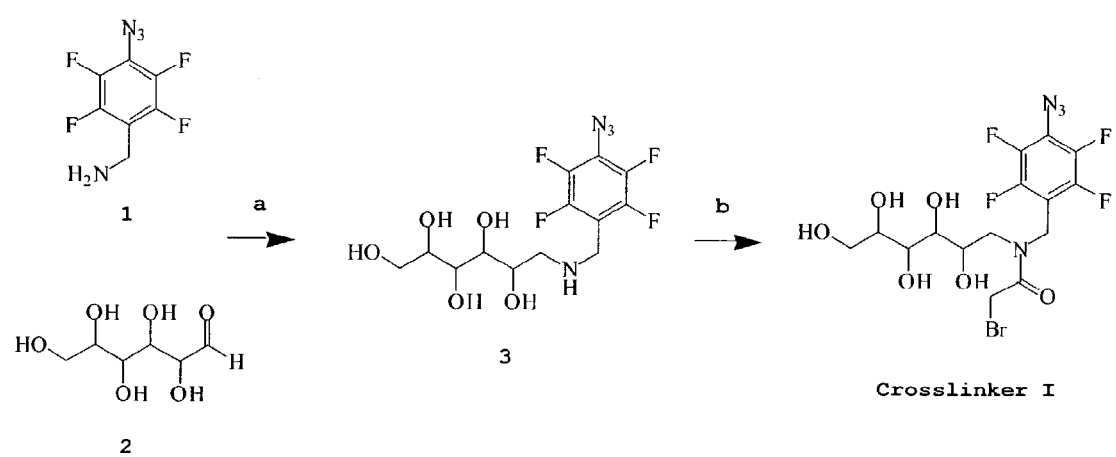
FIG. 10 is an illustration of chemical structures of a crosslinker for use in MXLINK methods, and how it may be made.
Figure 11:
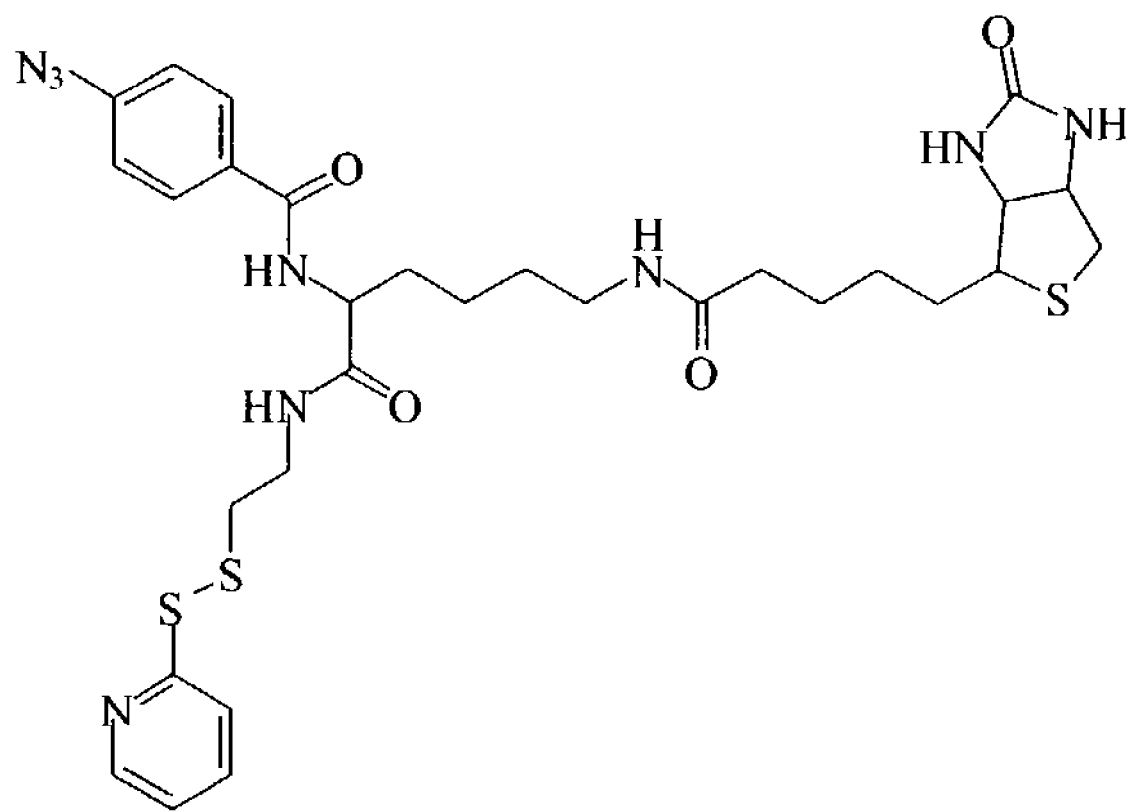
FIG. 11 is an illustration of a chemical structure of a crosslinker for use in MXLINK methods.

Exemplary crosslinking agents for use in MXLINK methods are shown in FIGS. 10 and 11.

Figure 12:
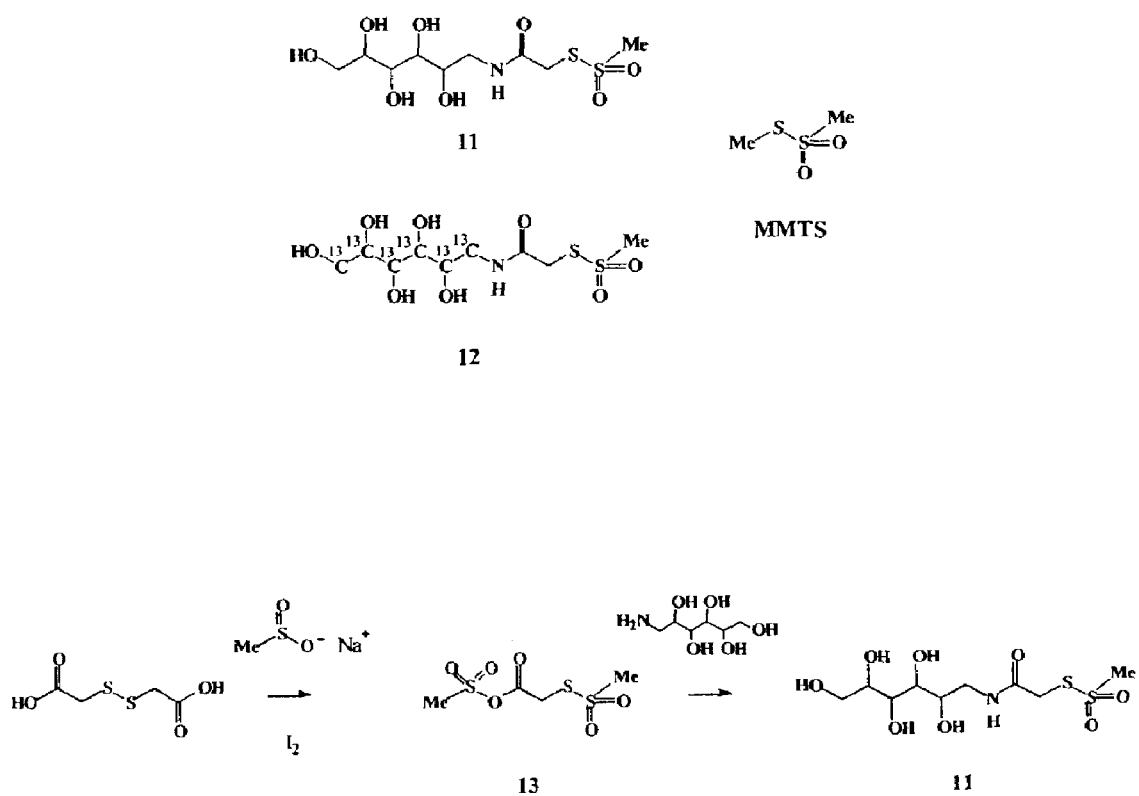
FIG. 12 is an illustration of chemical structures of compounds for use in MSX, and how they may be made.

Exemplary agents for use in MSX protocols are shown in FIG. 12.

Chemical Synthesis of CLRs

The chemical synthesis of CLRs in accordance with the invention may be carried out using a variety of synthetic techniques known in the art. Briefly, the aldehyde groups of isotope-labeled sugars can be reacted with 4-substituted benzylamines followed by reduction to form a secondary amine. The resulting secondary amines can then be reacted with iodo-alkyl substituted acid chlorides to form the corresponding N-iodoacyl amides as CLRs. The chemical synthesis of the CLRs is described in detail in Example 5. Alternate CLRs are easily synthesized using an identical protocol by substituting aldehyde, amine, and acid chloride or anhydride reagents.

Synthesis of thiol-specific, photoactivatable, and affinity tagged heterofunctional chemical crosslinking reagents generally comprises combining stoichiometric amounts of perfluoroaryl benzaldehyde and sodium azide dissolved in acetone and water, respectively, mixed and refluxed at 85° C. for 4 hours. The reaction is diluted with water, extracted with ether, the dried over magnesium sulfate, and dried by rotary evaporation. The azide is added para to the benzaldehyde. The desired product (37% yield) is purified by flash chromatography and confirmed by mass spectrometry and photoactivity. The p-azido-perfluorobenzaldehyde and glucamine are dissolved in stoichiometric amounts in water at 60° C., cooled and diluted with methanol to room temperature, forming the imine adduct. The imine is reduced gently by the addition of sodium cyanoborohydride in slight molar excess for 1 hour at room temperature, followed by 2-fold excess of hydrochloric acid. The solvent is evaporated under vacuum. The reaction is dissolved in methanol and redried repeatedly, removing the B(OCH3)3 side-product. The desired product N-p-azidoperfluorobenzyl glucamine (43% yield) is purified by flash chromatography and confirmed by mass spectrometry, and photoactivity.

Thiol activity is added in the following reaction. N-p-azidoperfluorobenzyl glucamine is dissolved in water with 5-fold molar excess of sodium carbonate. Iodoacetyl chloride is dissolved in dry dioxane and added to the glucamine solution at room temperature to molar amounts equivalent with the glucamine and mixed for 10 minutes. The reaction is extracted twice with chloroform and the aquaeous phase is acidified with hydrochloric acid. Residual chloroform is removed by centrifugation, the solution is 0.2 mm filtered and the product is purified by reversed-phase HPLC over C18 column.

Refering to FIGS. 10 and 11, exemplary CLRs that are useful in MXLINK may be made using the following methods. One of skill in the art would recognize that these methods could be adapted to synthesize CLRs not shown in FIGS. 10 and 11. Synthesis of N-(4-azido-2,3,5,6-tetrafluorobenzyl), N-(bromoacetyl) glucamine (Crosslinker I in FIG. 10): Step a: Adapted from Silverman & Harbury. (2002) *Journal of Biological Chemistry*, 277, 30968-30975. 4-azido-2,3,5,6-tetrafluorobenzylamine (1) is synthesized as described in Keana & Cai. (1990) *Journal of Organic Chemistry*, 55(11), 3640-3647. Glucose (2) is obtained comercially. 5 g (22 mmol) 4-azido-2,3,5,6-tetrafluorobenzylamine and 4 g (22 mmol) glucose were mixed at 65° C. 1.3 mL $H_2O$ was added, followed by dropwise addition of 3.9 mL of freshly distilled methanol. After the glucose had dissolved, the reaction was diluted with 39 mL freshly distilled methanol and cooled to 40° C. 1.6 g (25 mmol) of sodium cyanoborohydride was added and stirred at 40° C. for 1 hour. The reaction was acidified with 3.8 mL (44 mmol) of HCl. The solvent was removed under reduced pressure. For three times, the product was dissolved in 75 mL MeOH and redried. Finally, the pellet was resuspended in 22 mL MeOH, filtered, and dried. 7.2 g of a white solid was isolated (85% yield). Step b in the method is adapted from Silverman & Harbury (2002) *Journal of Biological Chemistry*, 277, 30968-30975. Bromoacetyl chloride is obtained comercially. 384 mg (1 mmol) of N-(4-azido-2,3,5,6-tetrafluorobenzyl) glucamine was dissolved in 5 mL of 0.5 M sodium carbonate. 120 uL of bromoacetyl chloride (1.1 mmol) diluted in 1 mL freshly distilled dioxane was added slowly at room temperature and the reaction was stirred for 15 minutes. The reaction was washed with chloroform and the organic phases were discarded. The reaction was then acidified with HCl and washed with chloroform until colorless. The organic phases were discarded. The aqueous phase was filtered with a 0.2 um syringe filter. Purification of the product by reverse-phase HPLC on a preparative C18 column (Varian-Dynamax 250× 41.4) using a gradient of 0-60% acetonitrile in 0.1% trifluoroacetic acid over 60 minutes at 20 mL/min produced a major peak eluting at 45% acetonitrile. This product peak was collected and the solvent was removed under reduced pressure. The yield of purified N-(4-azido-2,3,5,6-tetrafluorobenzyl), N-(bromoacetyl) glucamine was 260 mg (47%).

Crosslinker II may be made by known methods, such as those described in Alley et al (J. Am. Chem. Soc. 122:6126-6127, 2000).

The synthetic strategy is modular, so that the crosslinkers can be changed to alter the cysteine reactive chemistry (for example replacement of the iodoacetyl function with an activated disulfide), the affinity tag (for example replacement of glucose with biotin), the crosslinking chemistry, and the water solubility.

Referring to FIG. 12, CLRs that are useful in MSX may be made using the following methods. Thiosulfonate reagents for use in MSX may be prepared in two steps from inexpensive and commercially available starting materials. In the first step, compound 13 may be synthesized in methylene chloride from thioglycolyic acid disulfide, sodium methylsulfite and iodine(Fujiki, Synthesis, 2002(3): p. 343-8). In the second step, compound 13 is coupled to glucamine in dioxane to produce N-(1-thanethiosulfonylacetyl)-glucamine (MTSAG, 11). The gel strategy will utilize MTSAG and commercially available methyl-methanethiosulfonate (MMTS).

Mass spectrometry experiments may require $^{13}C$ labeled MTSAG (13C-MTSAG). $^{13}C$-MTSAG may be synthesized identically to MTSAG, except that $^{13}C$-glucamine is substituted for $^{12}C$-glucamine. $^{13}C$-glucamine is prepared by reductive amination of commercially available $^{13}C$-glucose (Wolfrom,. J. Org. Chem., 1958. 23: p. 571-5). Many MPAX and MSX reagents are based on $^{13}C$-glucose because it is one of the cheapest commercially available isotopically labeled compounds. Of course, other detectable reagents may be used.

Methods of Use of CLRs in Protein Structure Analysis

The CLRs of the invention can be used to determine the structural environment of cysteine residues (e.g., misincorporated cysteine residues) within a protein by mass spectroscopy. The use of the CLRs allows for the rapid analysis of protein structure.

In some embodiments, the CLRs are used to measure the protection factors of misincorporated cysteines in a protein of interest. The protection factor is defined as the intrinsic rate of reaction of the cysteine thiol in the unfolded protein divided by the rate of reaction of the cysteine thiol in the folded protein. Protection factors are measured by the analysis of CLR-modified protein fragments by mass spectrometry to determine the rate of reaction at each cysteine residue. After alkylation with CLR(s), the protein is fragmented by proteolysis by chemical and/or enzymatic cleavage, and peptides containing alkylated cysteine residues are purified by boronate affinity chromatography. The purified peptides are separated by reverse-phase chromatography, and analyzed by mass spectrometry. Peptides are identified by absolute mass and by mass fragmentation pattern.

Pulse chase experiments, which involve exposing the protein of interest to a CLR with one carbon isotope such as 13C, for a certain length of time followed by exposure to a CLR of a different carbon isotope, such as 12C allows for the determination of which misincorporated cysteines are solvent accessible and which cysteines are protected from the CLR alkylation for a longer period of time. In some instances the second CLR isotope is added under protein denaturation conditions to expose all of the misincorporated cysteines not alkylated by the first CLR.

In other embodiments, the first CLR (e.g.,. 13C) may be added in the presence or absence of a substrate, drug, inhibitory molecule or protein subunit to investigate which misincorporated cysteine are involved in a binding site of the protein and/or involved in protein-protein interactions. The sample is then exposed to the second CLR (e.g.,. $^{12}$C) under denaturing conditions. In certain instances, the protein of interest may be purified from the substrates or interacting proteins prior to denaturation and exposure to the second CLR. The samples are then proteolyzed and the amount of labeling of the misincorporated cysteines by the first CLR in the presence and absence of the substrate, drug, inhibitory molecule or protein subunit are compared. Amino acid residues involved in specific binding sites or regions of the protein of interest are identified by a change in apparent solvent accessibility upon addition of the substrate, drug, inhibitory molecule or protein subunit.

In other embodiments, the CLRs can be used to alkylate cysteine residues and also to crosslink the modified cysteine to nearby amino acid functional groups. Crosslinking CLRs not only allow for determining the protection factors of the misincorporated cysteines but also help to identify regions or amino acid sequences of the protein of interest which are near the misincorporated cysteines, further resolving the three-dimensional structure of the protein. Once pairwise relationships between misincorporated, cysteines and proximal amino acids have been determined, the three dimensional structure of the protein may be determined using any suitable software.

The CLRs of the invention can also be used for tracking differential expression levels of proteins in cellular extracts. These reagents can be used for any application which requires comparison of the relative number of cysteine-containing protein molecules in two defined states. It should be noted that experiments may be conducted with more than two different isotope labels (e.g. 12C, 13C, and 14C; 12C, 13C, and 2H; or 13C3, 13C6, 13C62H6) to allow for the comparison multiple protein states.

Mass spectrometry analysis provides a high-throughput readout that does not require the removal of native cysteines from the protein. The CLR-based detection method and the modular design of the misincorporation plasmids are well suited for proteome-wide studies.

Kits

The ordinarily skilled artisan upon reading the present specification can readily design kits for use in protein structure analysis. Such protein structure analysis kits can comprise, for example, at least one construct for the expression of a cysteine misincorporator tRNA (e.g. pMPAX or yMPAX) and a host cell which can be co-transformed by the pMPAX construct and a construct configured to express the protein of interest (e.g., having a cassette for ready insertion of a nucleic acid encoding a protein of interest, and expression of the protein in the host cell). The kit may comprise additional pMPAX constructs for the misincorporation of cysteine for various amino acids or codons.

The kit may in addition or alternatively comprise an alkylating agent for the alkylation of misincorporated cysteine residues, or an MSX agent for disulfide bond formation, or a MXLINK crosslinking agent, as well as chemical compounds or enzymes for the proteolytic cleavage of the protein of interest in various states (e.g. native, denatured, misincorporated, alkylated and/or the presence or absence of binding compounds such as substrates). Instructions for carrying out the protein footprinting method and/or structural analyses methods of the invention may also be included in a kit.

In certain embodiments, the alkylating agent may be a CLR of the invention. The kit may comprise two CLRs of identical structure except for one being composed of $^{12}$C and the other enriched in $^{13}$C. Boronate affinity resin and associated buffers and reagents may also be included. Instructions on the method of use of the CLRs, as well as the mass spectrometry analysis of peptide fragments generated from the protein of interest which are covalently bonded to a CLR molecule, may also be included. An exemplary CLR for LC/MS analysis includes an N-(iodoacetyl, p-chlorobenzyl)-glucamine. The kit may also comprise instructions for instrument calibration, sample preparation and protocols for completing the protein footprinting analysis and data interpretation. The kit can further comprise solutions for the preparation of biological samples for the protein structure analysis. In certain embodiments, the CLR may be a crosslinking agent containing an azide or active ester. Suitable crosslinkers for use in the subject kits are shown in FIGS. 10 and 11, although others are known in the art.

In other embodiments, the protein of interest may be tagged with amino acid sequences allowing its detection and/or purification (eg., a protein kinase A site and a 6×His tag (a polymer of six histidine residues)) incorporated in the expression vector included in the kit. In this example, the kit may comprise a nickel resin and buffers to purify the protein using the 6×His tag and enzyme and reagents required to label the protein at the protein kinase A site. Other affinity tags and labeling motifs are possible.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods were utilized in Examples 1-5 and are exemplary procedures for carrying out the MPAX method of the present invention Misincorporation of cysteine. The native E. coli cysteine tRNA was cloned under the control of the T7 promoter of the pET21a plasmid (Novagen, Madison, Wis.), and the native E. coli cysteinyl tRNA synthetase was cloned into the BglII and SphI sites of the same plasmid to generate pMPAX. Derivative misincorporator plasmids were generated by Kunkel mutagenesis (Kunkel, T. A., et. al., Methods Enzymol. 204:125, 1991) of the tRNA anti-codon sequence and named pMPAX[ABC] where ABC denotes the mutant anti-codon triplet. The yeast trisosephosphate isomerase (TIM) gene (Silverman, J. A., et. al., Proc. Natl. Acad. Sci. U.S.A. 98:3092, 2001) was amplified by PCR, adding a C-terminal protein kinase A tag (amino acid sequence: GRRASIY), and cloned into the EcoRI and HindIII sites of pET28a (Novagen, Madison, Wis.). The two native cysteines were substituted by Kunkel mutagenesis to generate the C41V/C126A double mutant designated pH6_TIM_PKA. BL21 (DE3) cells were co-transformned with pH6_TIM_PKA and the pMPAX derivative of interest. Cultures were grown in M63 media (Ausubel, F. M. et al., Eds., Current Protocols in Molecular Biology, vol. 1 (John Wiley & Sons, New York, 1995)) containing 50 µg/mL ampicillin and 20 µg/mL kanamycin and induced overnight by addition of IPTG to 1 mM.

A more detailed description of the protocol utilized in the construction of the MPAX constructs is given below:

Preparation of single-stranded DNA. Transfonm plasmid of interest containing an F1 origin of replication into dut-ung-JM109 cells. Plate onto LB media containing appropriate antibiotics and incubate at 37° C. overnight. A single colony is picked into 5 mL 2XTYP media containing the appropriate antibiotic. The cells are grown in shaking culture at 37° C. until the cells reach saturation (8-10 hours). 100 µL cells is added to 10 mL 2XTYP media in a 100 mL flask, and the culture maintained in a shaking incubator at 37° C. for 30 minutes. 80 µL helper phage (Promega) is added, followed by 100 µL 2 M K2HPO4, and the culture maintained at 37° C. in a shaking incubator overnight. The cells are centrifuged at 45,000×g for 15 minutes, the supernatant collected, and centrifugation repeated. Approximately 0.25 volumes of phage precipitation solution is added, and incubated on ice for 30 minutes, followed by centrifugation at 45,000×g for 30 minutes. The supernatant is discarded, and the pellet resuspended in 400 µL dH2O.

The sample is then extracted with tris saturated phenol/chloroform/iso-amyl alcohol (25:24:1), and the extraction repeated until there is no visible material at the interface. Single-stranded (ssDNA) is precipitated with 0.1 volumes of 3 M sodium acetate pH 5.2 and 2.5 volumes of cold ethanol, followed by centrifugation at 14,000×g for 30 minutes. The pellet is washed with 70% ethanol, and dried under vacuum. The pellet is then resuspend in 200 µL dH2O or TE. Gel purification of the ssDNA can be used to reduce background. However, crude ssDNA can be used with no further purification with good results in most cases.

Buffers used in the above protocol were; 2XTYP Media- 16 g yeast extract, 5 g NaCl, 2.5 g $K_2HPO_4$, $dH_2O$ to 1 liter and autoclave. Phage precipitation solution-3.75 M ammonium acetate pH 7.5, 20% PEG-8000.

Mutagenesis protocol. Mutagenesis was performed based on a protocol adapted from the method of Kunkel et. al.(1991) Methods Enzymol. 204 125-139. In general, the mutagenic sequence is flanked on either side by 15 base pairs of complementary sequence. Be sure the oligo is complementary to the ssDNA template!

To alter the anti-codon sequence of the tRNA, the following oligo is used: 5'-CGGACTAGACGGATTXYZ-AATCCGCTACATA-3' (SEQ ID NO:2)

where XYZ is the new codon sequence (Valine codon GTC, anti-codon GAC). To create mutants of AmiE at C165, the following oligo is used: 5'-GTTTCTTTGATTATTXYZ-GATGATGGAAACTAC-3' (SEQ ID NO:3) where XYZ is the new codon sequence (Valine codon GTC, anti-codon GAC).

Phosphorylation of the oligo was carried by the following protocol: 1 µL 5 µM mutagenic oligo was added to 1 µL 1 M Tris pH 7.5, 1 µL 0.1 M DTT, 2 µL 0.1 M $MgCl_2$, 2 µL 10 mM ATP, 0.2 µL 10 U/µL T4 polynucleotide kinase, 12.8 µL $dH_2O$ and incubated 1 hour at 37° C. After incubation, 3 µL 100 mM EDTA was added to the mixture and incubated for 10 minutes at 65° C. Then 1 µL of single stranded plasmid DNA and 1.2 µL 20×SSC was added and placed in a heat block at 65° C., and cooled to room temperature over ~1 hour. The following mixture was then added: 2 µL 1 M Tris pH 8.0, 2 µL 0.1 M DTT, 1 µL 1 M $MgCl_2$, 1 µL 100 mM ATP, 1 µL 10 mg/mL BSA, 5 µL 10 mM dNTP mix, 1 µL 20 U/µL T4 DNA ligase, 1 µL 10 U/µL T4 DNA polymerase, 65 µL dH2O. The mixture was incubateed 5 minutes on ice, 5 minutes at room temperature, 3 hours at 37° C. (overnight incubation is required in certain cases), followed by the addition of 100 µL $dH_2O$ and extracted with phenol/chloroform, and ethanol precipitation of the DNA.

The oligo was transformed into XL1 Blue, DH5-α, or other suitable cloning cells.

A Miniprep DNA from the colonies was completed and screened for mutation by sequencing. The following primers are used for sequencing:

```
pSX R-seq      5'-TTCCTTTCGGGCTTTGTTAGC-3' pAmiE M-seq    5'-GACAGCGCACAATGAGTTCTG-3'
```

NTCB cleavage. Approximately 10 µg of purified protein was radioactively labeled by incubation with ATP-γ-$^{33}$P and protein kinase A (Sigma, St. Louis, Mo.). Alkylation of cysteines was accomplished by incubating the protein in 50 mM sodium bicine pH 8.6, 10 mM iodoacetamide for 2 minutes. All experiments were conducted at room temperature. The reaction was quenched by addition of an equal volume of 20 mM β-mercaptoethanol, 0.1 mg/mL BSA. NTCB cleavage at cysteine residues was performed as described (Jacobson, G. R., et al J. Biol. Chem. 248:6583, 1973; Wu, J. T., Anal. Biochem. 258:268, 1998) with several modifications. An equal volume of 8 M guanidinium chloride, 300 mM sodium bicine pH 8.6, 100 mM NTCB was added to the protein sample and incubated for 5 minutes. Cyanylated proteins were TCA precipitated (Arnold U., R. Ulbrich-Hofmann, Anal. Biochem. 271:197, 1999) and the pellet was resuspended in 10 µL 8 M urea, 0.1 M NH$_4$OH. After a one hour incubation, 5 µL of 500 mM Tris chloride pH 6.5, 25% glycerol, 5% SDS, 0.001% Coomassie Brilliant Blue G250 was added to quench the cleavage and the resultant solution was loaded directly onto a tricine gel (Schagger H., G. von Jagow, Anal. Biochem. 166:368, 1987) with an additional comb gel layer (Wiltfang J., et. al., Electrophoresis 12:352, 1991). This protocol resulted in an average cleavage efficiency of 84%. The molecular weight markers were constructed by creating a series of single cysteine mutants of TIM by Kunkel mutagenesis. The pooled proteins were cleaved with NTCB to generate a ladder of defined peptides. Gels were run at 140-160 volts overnight, then transferred onto Whatman 3MM Chr paper and dried. Gels were exposed on image plates and quantitated on a Phosphorimager (Molecular Dynamics, Sunnyvale, Calif.).

Substrate binding. Labeled protein misincorporated at leucine or valine was incubated with or without 50 mM sodium glyceraldehyde-3-phosphate in 200 mM sodium bicine pH 8.6, 10 mM iodoacetamide for 2 minutes before quenching and cleavage. Illustrations were generated using MOLSCRIPT (Kraulis P. J., *Journal of Applied Crystallography* 24:946, 1991) and the 7TIM structure[Davenport, 1991 #11 R. C. Davenport et al., *Biochemistry* 30:5821, 1991).

Antibody binding. The myc epitope sequence [EQKLI-SEEDL] was inserted at position 132 in the yeast TIM sequence by Kunkel mutagenesis. The denatured protein was diluted from 5 M urea into a reaction containing a final concentration of 1 M urea, 50 mM sodium bicine pH 8.6, 150 mM NaCl with or without 1 µL of polyclonal anti-myc serum and incubated with 10 mM iodoacetamide for 2 minutes.

Measurement of protection factors. Labeled protein was prepared and incubated for 24 hours with 50 mM sodium bicine pH 8.6, 10 mM iodoacetamide. Samples were withdrawn at various timepoints, acid-quenched, and stored at −20° C. until they could be analyzed. The protection factor at each position was defined as the ratio of the observed rate of alkylation in the unfolded state to the observed rate of alkylation in the folded protein. Results are the average of three independent measurements. Alkylation rates in the unfolded state were measured to be $3.3 \pm 0.1$ $M^{-1}sec^{-1}$ in 4 M GdmCl, 50 mM sodium bicine pH 8.6, 25° C. for all probes. This value was corrected to 1.5 $M^{-1}sec^{-1}$ for denaturant-free buffer based on the effect of GdmCl on the alkylation rate of glutathione (data not shown). All alkylation rates were found to depend on the concentration of alkylating reagent, confinning that alkylation occurs by the EX2 mechanism. The fractional burial of each side-chain was calculated using X-PLOR (Brunger A., *X-PLOR: A system for X-ray Crystallography and NMR* (Yale University Press, New Haven, 1992) and the 7TIM structure. To determine the stability of TIM, labeled protein at a final concentration of 2 µM was incubated with 50 mM sodium bicine pH 8.6, 10 mM iodoacetamide for 5 hours in the presence of 0.7-1.1 molar GdmCl (in 0.1 molar increments). The values of RT*ln (protection factor) for valine 91 were plotted against denaturant concentration and extrapolated linearly to zero. The unfolding free energy of TIM was evaluated as the y-intercept.

Selection for misincorporation. The *H. pylori* amidase AmiE was amplified from genomic DNA by PCR and cloned between the BglII and SphI sites of pET24a (Novagen, Madison, Wis.) to generate pAmiE. Mutations at C165 were created by Kunkel mutagenesis. Mutant pMPAX libraries were generated by treating 10 µg of pMPAX[GUG] or PMPAX[GCU] DNA with ultraviolet light in a Stratalinker (Stratagene, La Jolla, Calif.) for 30 seconds. The libraries were transformed into BL21(DE3) Tuner cells (Novagen, Madison, Wis.) containing pAmiE with either a C165S or a C165H mutation, resulting in $10^5$-$10^6$ transformants. pMPAX plasmids from cells that grew faster than the parent plasmid in acetamide media (50 mM potassium phosphate pH 7.8, 10 mM glucose, 1 mM $MgCl_2$, 100 µM citric acid, 50 µM $FeCl_3$, 25 µM $MnCl_2$, 25 µM $CaCl_2$, 100 mM acetamide, 25 µM IPTG, 50 µg/mL ampicillin, and 20 µg/mL kanamycin) were isolated, co-transformed with pH6_TIM_PKA, and screened for misincorporation efficiency.

Readout by mass-spectrometry. Wild-type TIM was incubated with 10 mM $^{13}$C-CLR, 50 mM sodium bicine pH 8.6 at room temperature for 10, 300, or 1440 minutes. $^{12}$C-CLR was added to 100 mM, followed by guanidinium chloride to 4 M. The reactions were incubated for a further 45 minutes. In parallel, two samples of wild-type TIM were treated respectively with 100 mM of $^{13}$C-CLR or $^{12}$C-CLR in 100 mM sodium bicine pH 8.6, 4 M guanidinium chloride for 1 hour, then pooled to generate a control sample with a 1:1 ratio of $^{12}$C:$^{13}$C at each misincorporated cysteine. Samples were TCA precipitated to remove excess alkylating reagents and resuspended in 5 M urea. The urea was diluted to 0.5 M in 100 mM Tris chloride pH 8.0, 25 µg/mL sequencing-grade trypsin (Roche, Basel, Switzerland), and the protein digested overnight at 37° C. Insoluble material was removed by centrifugation and the supernatant added to 250 µL phenylboronate acrylamide beads (Pierce, Rockford, Ill.) pre-equilibrated in binding buffer (50 mM sodium HEPES pH 9.0, 500 mM NaF, 10% acetonitrile). The mixture was rotated for 30 minutes, then washed for three 30-minute incubations with 1 mL binding buffer to remove unbound material. Modified peptides were eluted by two 15-minute incubations with 250 µL elution buffer (10 mM Tris chloride pH 8.0, 100 mM sorbitol, 10% acetonitrile). The eluates were pooled and concentrated under vacuum to ~50 µL total volume. 40 µL was injected onto a 1 mm×50 mm C18 column (Michrom, Auburn, Calif.) in buffer A (0.025% trifluoroacetic acid, 0.1% formic acid in water) and eluted in a linear gradient of 5-70% buffer B (0.022% trifluoroacetic acid, 0.085% formic acid in acetonitrile) over 50 minutes. Eluting peptides were analyzed by tandem mass spectrometry on an LCQ ion trap mass spectrometer as described by Gygi, S. P., et al., *Nat. Biotechnol.* 17:994, 1999. No difference in the elution times of the $^{13}$C-CLR or $^{12}$C-CLR modified peptides was observed. The entire peak area was integrated for calculation of the mass ratio.

Chemical synthesis of cysteine labeling reagent compounds. The CLR compounds were prepared by N-acylation of a N-p-chlorobenzyl-glucamine precursor to provide the N-iodoacetyl, p-chlorobenzyl $^{13}$C- and $^{12}$C-glucamines.

N-p-chlorobenzyl-glucamine. The following synthesis of N-p-chlorobenzyl-glucamine is a modification of the synthesis described by Norrild, et. al. (1996) Carb. Res. 291 85-98 and Kagan, et. al. (1957) J. Am. Chem. Soc. 79 3541-3544. 15 mmol (3.0 g) glucose was added to a 100 mL round-bottom flask as wells as 15 mmol (1.82 mL) 4-chlorobenzylamine (Aldrich, St. Louis, Mo.) and 0.9 mL $dH_2O$. The mixture was heated in a water bath at 60° C. until the mixture was in solution. 2.7 mL methanol was added and the mixture was allowed to cool to room temperature. Once the solution had cooled an additional 27 mL methanol and 18 mmol (0.7 g) $NaBH_4$ was added. The mixture was stirred for 1 hour at room temperature with the flask unsealed. 30 mmol HCl (2.5 mL) was added to acidify the solution and the solvent was evaporated under vacuum. 50 mL of methanol was added to resuspend residue, and the solvent was again evaporated under vacuum. The above step was repeated twice more, for a total of three methanol additions. This step allows evaporation of the $B(OCH_3)_3$ side-product. 15 mL methanol was added to resuspend the residue and filtered. This wash step was repeated once. The filtrates were pooled and dried under vacuum. Exemplary yields are around 3.8 gm (74%) of white solid. The $^{13}$C-labeled version was synthesized identically as above, substituting $^{13}C_6$-glucose (>99% isotopic purity; IsoTec, Miamisburg, Ohio).

N-(iodoacetyl, p-chlorobenzyl)-glucamine. N-(iodoacetyl, p-chlorobenzyl)-glucamine isotopic protein labeling reagents were synthesized in the following manner.

1 mmol (340 mg) N-p-chlorobenzyl-glucamine was added to a 50 mL round-bottom flask and 5 mL 1 M $Na_2CO_3$, pH 10 was added to the N-p-chlorobenzyl-glucamine and stirred until the solids have dissolved. 1.2 mmol (110 µL) iodoacetyl chloride (Lancaster Synthesis, Windham, N.H.) was dissolved into 5 mL dry dioxane and the iodoacetyl chloride solution was added to the flask with rapid stirring and incubating for 10 minutes at room temperature. The reaction was extracted twice against chloroform, keeping the aqueous phase. HCl was added to acidify the solution followed by chloroform extraction until the aqueous phase was colorless. The aqueous phase was transferred to a 15 mL Falcon tube and centrifuged 15 minutes at 4000×g to remove residual chloroform. The supernatant was filtered through a 0.2 µm syringe-tip filter and the product was purified by reverse-phase HPLC on a semi-prep C18 column (Vydac, Hesperia, Calif.) using a gradient of 0-40% acetonitrile in 0.1% trifluoroacetic acid over 30 minutes at 2.5 mL/min. The major peak (~30% acetonitrile) was collected and lyophilized. An exemplary yield is approximately 382 mg or 81%.

The $^{13}C$-labeled version was synthesized identically as above, substituting N-p-chlorobenzyl-$^{13}C_6$-glucamine.

The reagents are referred to as $^{12}C$-CLR or $^{13}C$-CLR depending on the isotope labeling of the glucose precursor. Reagents were stored dry at 4° C. until ready for use. Stock solutions were prepared in 0.1% TFA, 25% acetonitrile and the concentration determined by alkylation of a modified glutathione derivative. Stock solutions were stored up to 2 weeks at −20° C. with no apparent breakdown.

Example 1

Misincorporation of Cysteine for Protein Footprinting

A cysteine-free variant of yeast triosephosphate isomerase (TIM) was used as a model system to investigate the MPAX technique. TIM is a dimeric $(\beta/\alpha)_8$ barrel protein. The TIM construct used here includes a C-terminal protein kinase A tag to allow labeling with radioactive phosphate, and an N-terminal 6×His tag on a 30 amino acid linker for purification. This linker shifts the full-length, 290-residue protein away from the fainter cleavage products during gel electrophoresis.

Figure 3:
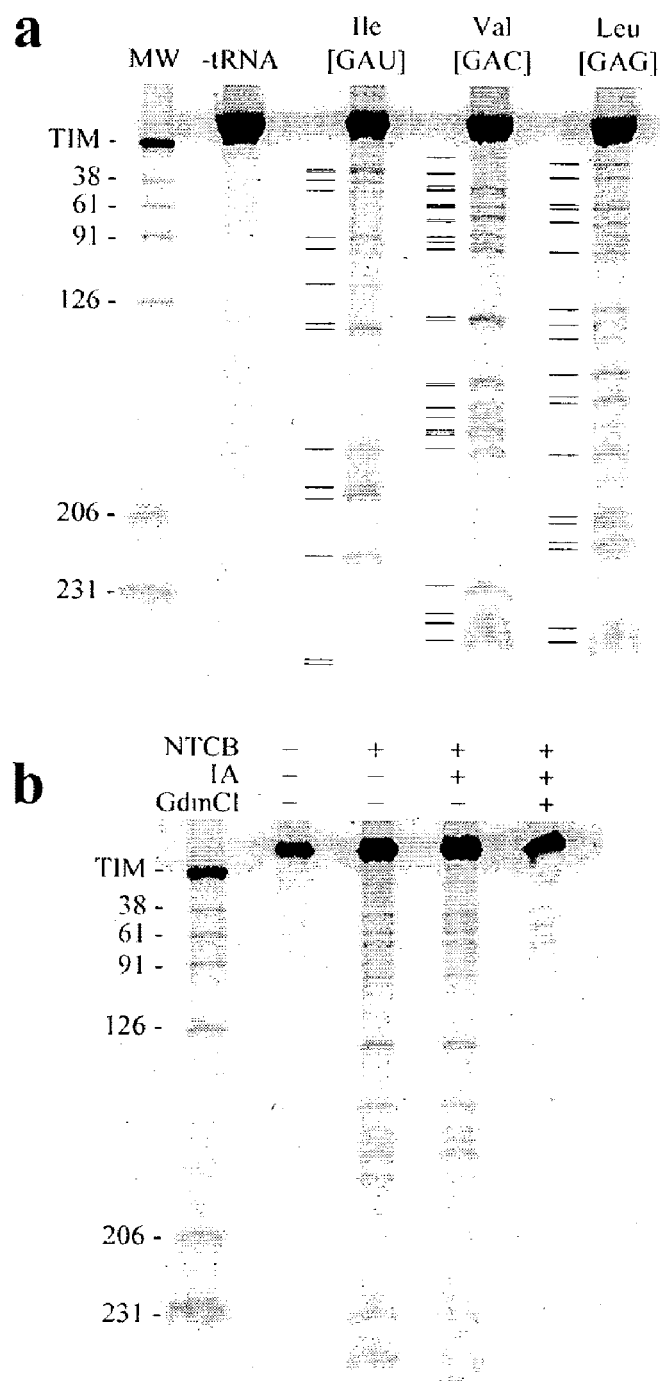
FIG. 3 includes panels A and B.

The misincorporation of cysteine at specific amino acid positions was first verified by expressing TIM in the presence or absence of a series of cysteine misincorporator tRNAs. Cleavage of TIM by NTCB was observed only when TIM was co-expressed with a misincorporator tRNA (FIG. 3, panel A). FIG. 3, panel A is an autoradiograph of an electrophoretic gel which shows that the TIM protein was expressed in the presence of the indicated misincorporator tRNA (Ile, Val or Lue) and labeled at its C-terminus with radioactive phosphate. The labeled protein was then cleaved with NTCB. The expected pattern of cleavage is shown as black lines to the left of each lane. MW denotes the molecular weight markers, which are labeled according to the residue cleaved in the TIM protein. The position of the full-length protein is designated as TIM. The observed ladder of cleavage bands depends on the anti-codon sequence of the tRNA, and corresponds to the pattern expected based on the amino acid sequence of TIM (FIG. 3. panel A).

Amino acid analysis confirmed the presence of low levels of cysteine (~0.3 cysteines/protein) in the purified proteins. FIG. 3, panel B is an autoradiograph of an electrophoretic gel which shows the fragments formed by NTCB cleavage of TIM with cysteine misincorporated at valine positions when treated with 10 mM iodoacetamide (IA) for two minutes in the presence or absence of 4 M guanidinium chloride (GdmCl). Treatment of the protein with 10 mM iodoacetamide for two minutes under denaturing conditions completely blocked cleavage at misincorporated cysteines (FIG. 3, panel B). However, treatment of the protein with iodoacetamide under native conditions did not block cleavage at most sites. The data suggest that protein structure protects these residues from alkylation.

A concern regarding the use of misincorporated cysteines as a probe of protein structure is that a cysteine mutation itself could disrupt the native conformation. This concern is mitigated by the fact that the cysteine side chain is small and amphiphilic, and thus a good substitute for many amino acids. To address the question directly, the effects on in vivo folding caused by cysteine replacements at the isoleucine, leucine, and valine residues of triosephosphate isomerase was measured. TIM was expressed in the presence of misincorporator tRNAs and was purified from both soluble and inclusion body fractions of *E. coli*. The level of misincorporation at each position was measured by NTCB cleavage. The cleavage intensity in the two protein preparations was found to differ by no more than five-fold at any position (data not shown). The data indicate that none of the cysteine mutations causes a significant partitioning of triosephosphate isomerase into inclusion bodies in vivo, and hence suggests that cysteine mutations at these positions do not interfere substantially with folding.

Example 2

Mapping Binding Sites

Strategies for chemically mapping protein interaction sites fall into three broad categories: interference, crosslinking and protection (Creighton, T. E., *Proteins* (W. H. Freeman and Company, New York, 1993) pp. 333-334). Interference is based on scanning mutagenesis of a protein. If a residue substitution interferes with a physical interaction, it is inferred that the residue plays a role in binding. In the chemical crosslinking approach, residues that participate in crosslinks are identified, and the existence of the crosslink implies spatial proximity to the binding partner. Finally, protection methods are based on chemical modification of a protein in the presence and absence of a binding partner. Binding sites are identified as residues protected from modification by the presence of the partner. The three techniques provide distinct and complementary information. For example, protection and interference analysis identifies regions of a protein that undergo a conformational change upon binding, whereas crosslinking only maps direct contact surfaces. Each of the chemical mapping techniques can be carried out in conjunction with parallel misincorporation of cysteine residues. A protection analysis is described below, as it is particularly applicable to multiple proteins and multiple binding partners, we describe a protection experiment here.

Figure 4:
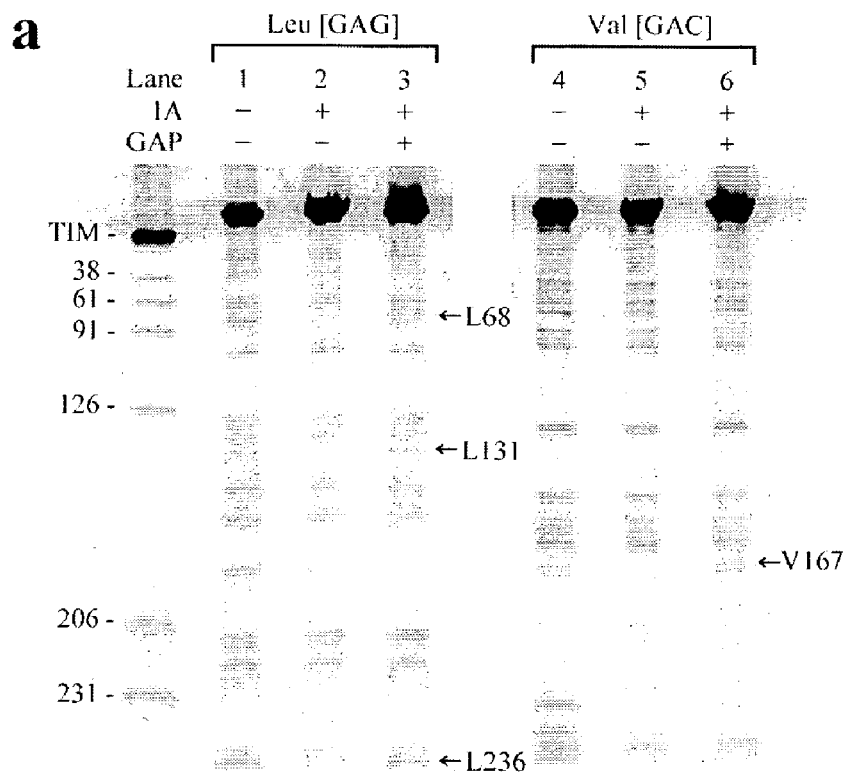
FIG. 4 includes panels A and B.
Figure 4:
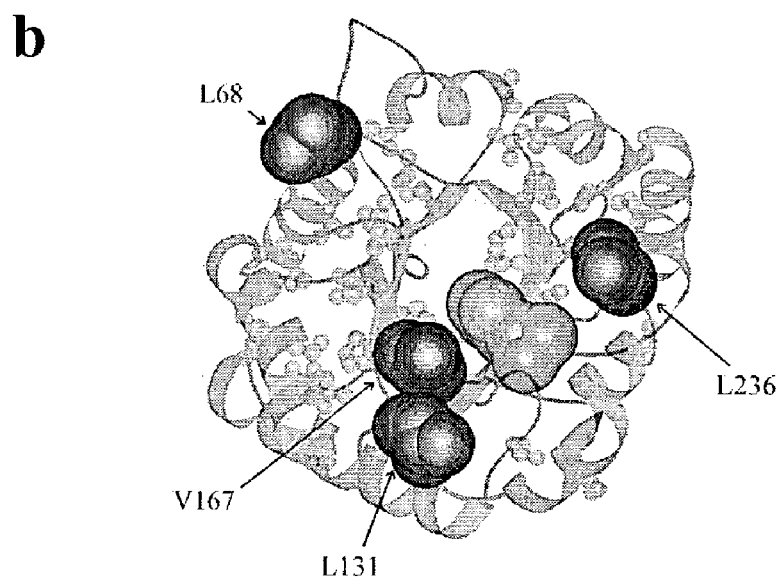

To footprint the ligand-binding site of triosephosphate isomerase (TIM) protein, misincorporated cysteines were alkylated with 10 mM iodoacetamide for two minutes in the presence and absence of 50 mM glyceraldehyde-3-phosphate, a TIM substrate. Binding of the substrate was found to protect specifically a subset of the fastest alkylating residue positions (FIG. 4, panel A). FIG. 3, panel A is an autoradiograph of a electrophoretic gel showing the NTCB fragment pattern of the TIM protein after treatment with 10 mM iodoacetamide (IA) for two minutes in the presence (lanes 3 and 6) or absence (lanes 2 and 5) of 50 mM glyceraldehyde-3-phosphate (GAP), a TIM substrate. The $K_M$ of TIM for GAP is 0.5 mM. Unalkylated protein is shown in lanes 1 and 4 for comparison.

Three of the "probes" are located in close proximity to the crystallographically determined substrate-binding site (FIG. 4, panel B), and correspond to the only solvent accessible (less than 99% buried) valine and leucine residues within 15 Å of the substrate. A fourth residue protected by the substrate is located in the dimerization loop, which makes contacts to the substrate in the opposite monomer. FIG. 4, panel B is a molecular model of the yeast TIM crystal structure showing the locations of amino acids protected from alkylation by the substrate, glyceraldehyde-3-phosphate. Positions protected by the substrate are shown as dark gray van der Waals surfaces, while those which show no protection are shown in light gray. The substrate analog is indicated by the arrow and is shown as a medium gray van der Waals surface.

Figure 5:
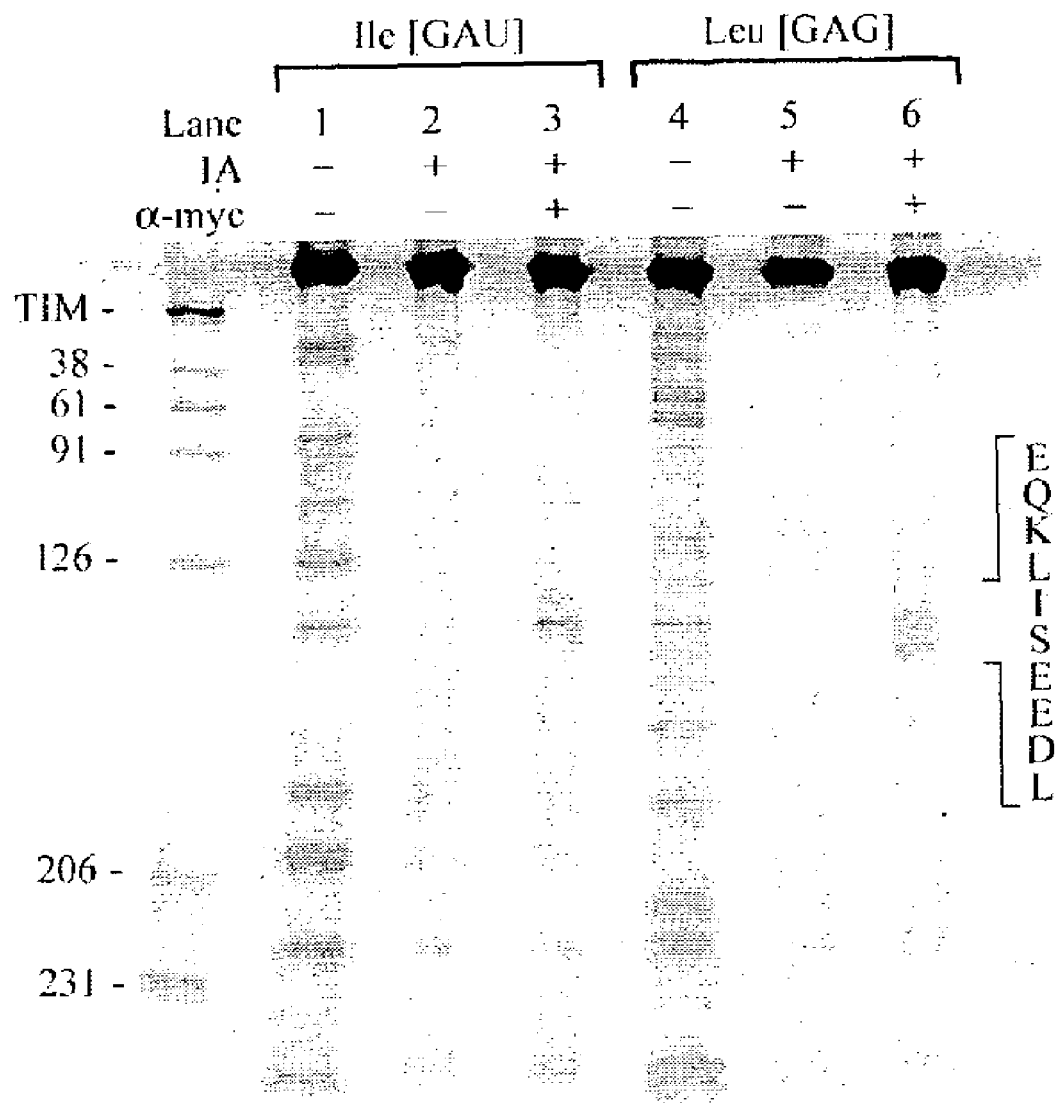
FIG. 5 is an autoradiograph of an electrophoretic gel of the NTCB fragment patterns of a TIM protein with a myc epitope tag sequence inserted into loop 5 of TIM in the presence or absence of a polyclonal rabbit serum inoculated against the myc tag (α-myc).

The utility of MPAX for mapping a protein-protein interaction surface was also investigated (FIG. 5). Because native triosephosphate isomerase (TIM) is a homodimer that does not interact with other protein partners, tagged variants of TIM with myc epitope insertions before or after the fifth helix of the barrel were created. The tagged proteins were unable to refold, so the antibody binding experiment was performed with denatured TIM. Anti-myc antibodies specifically protected from alkylation only cysteine residues misincorporated within the myc epitope, providing a direct mapping of the antibody-binding site. Alkylation at single amino acid resolution was observed by separating leucine and isoleucine bands in different gel lanes. FIG. 5 is an autoradiograph of an electrophoretic gel of the NTCB fragment patterns of a TIM protein which had a myc epitope tag sequence inserted into loop 5 of TIM (shown at right). The tagged protein was treated with 10 mM iodoacetainide (IA) for two minutes in the presence (lanes 3 and 6) or absence (lanes 2 and 5) of polyclonal rabbit serum inoculated against the myc tag (α-myc). The unalkylated protein (lanes 1 and 4) is shown for comparison. The three protected bands correspond to the leucine and isoleucine residues present in the epitope sequence.

The above data demonstrates the utility of the MPAX method for examining partially folded proteins. Importantly, a protein-binding interface was revealed in a single experiment.

Example 3

Mapping Protein Topology

Current de novo protein structure prediction algorithms yield multiple reasonable structural models given an input sequence. The inclusion of sparse experimental NMR data in the prediction process significantly improves the accuracy and convergence of the computed models (Bowers, P. M., et. al., J. Biomolecular NMR 18:311, 2000). To address the possibility that data derived from the MPAX method might also be useful for guiding computational structure predic-
tion, the inventors investigated whether the MPAX method could be used to map protein topology.

The alkylation rates of cysteine residues misincorporated at 61 positions in the TIM sequence were measured. Solvent exposed residues are expected to alkylate more rapidly than buried residues, and thus alkylation rates should be useful for assigning sequence positions to interior or exterior environments. The observed alkylation rates can be interpreted using a kinetic model derived from hydrogen exchange experiments (Bai Y., et. al., Science 269: 192, 1995). In this model, the solvent accessibility of each cysteine side chain is described by an equilibrium between unfolded, solvent-accessible states and a folded, solvent-inaccessible state (FIG. 1, panel C). Alkylation was assumed to occur only in the exposed states. The factor by which native protein structure slows alkylation of a cysteine residue (relative to the rate of alkylation of the same cysteine in the unfolded state) defines a protection factor for the site of misincorporation. Large protection factors indicate side-chain burial, and the magnitude of protection increases in proportion to local protein stability.

Figure 6:
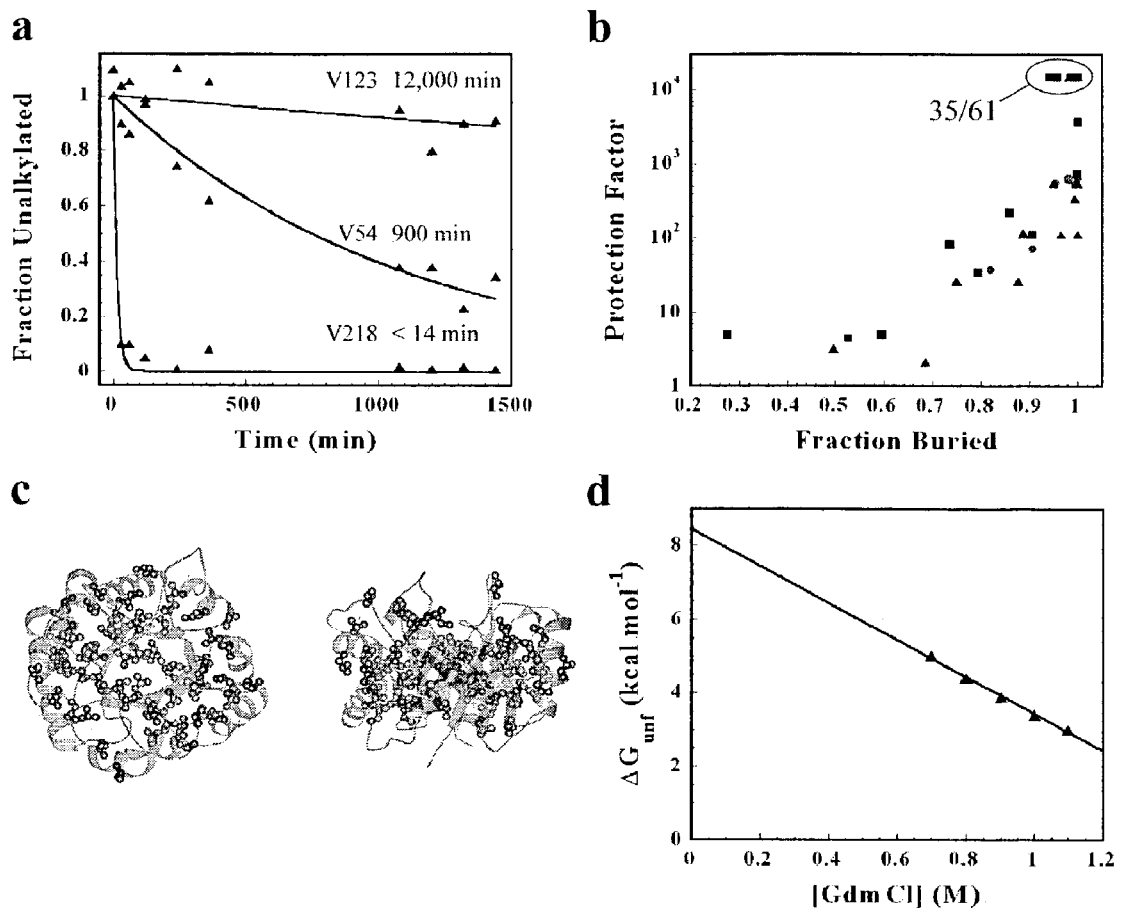
FIG. 6 includes panels A-D.

The extent to which protein structure slows the rate of alkylation was investigated at 61 positions in TIM and is shown in FIG. 6 panels A-D. TIM was alkylated with 10 mM iodoacetamide for variable time periods and then cleaved with NTCB. FIG. 6, panel A is a graph which shows representative data showing the fractional cleavage at three valine positions, 54, 123, 218, (substituted by cysteine) with respect to alkylation time. The solid lines represent an exponential fit of the data to a first-order kinetic model, and the half-life for each fit is indicated.

Protection factors were measured by incubating TIM for 24 hours under native conditions in the presence of 10 mM iodoacetamide. Samples were withdrawn periodically and analyzed by NTCB cleavage. This procedure allows accurate measurement of rates up to $10^4$-fold slower than the intrinsic alkylation rate (a protection factor of $10^4$). All side chains at sites displaying a protection factor greater than 103 are more than 94% buried in the crystal structure of the wild-type protein (FIG. 5, panels B and C). Conversely, all side chains at sites displaying protection factors less than 10 are at least 30% solvent accessible. The correlation between residue burial and protection shows that MPAX can be used to assign amino acid positions to the interior or exterior of a protein, providing a constraint on the topology of the protein backbone fold.

The protection factor at each misincorporation site is plotted against the fractional burial of the corresponding wild-type residue in the TIM crystal structure is shown in FIG. 6, panel B. Thirty-five of the sixty-one probes examined exhibit protection factors of 104 or greater (the limit of detection in this experiment) and overlap in the upper right-hand corner of the plot. Data are shown for isoleucine (closed circles), valine (closed triangles), and leucine (closed squares) positions.

FIG. 6, panel C shows models of the protein crystal structure. Residues with a protection factor less than 100 are colored towards the outside of the strucure, while residues with protection factors greater than 100 are usually in the inside of the structure. The highly protected, apparently solvent-exposed residue at the top of the protein (right) is buried in the dimer interface.

The equilibrium stability of TIM cannot be measured by spectroscopic methods because even moderate concentrations of the unfolded polypeptide aggregate. However, protection factors can provide a direct measure of protein stability under native conditions, when >99% of the protein is folded. The denaturant dependence of the protection factor for valine 91, one of the slowest exchanging residues in TIM, indicates that TIM is 8.5 kcal·mol$^{-1}$ stable at 2 μM concentration (FIG. 5, panel D). The unfolding free energy at valine 91 [calculated as RT*ln(protection factor)] is plotted as a function of GdmCl concentration as shown in FIG. 6, panel D. The solid line is a linear fit of the data extrapolated to zero denaturant. MPAX allows measurement of thermodynamic quantities for large and poorly folding proteins like TIM, permitting the kind of energetic analysis currently restricted to small model proteins.

Example 4

Misincorporation at Alternate Codons

For MPAX to be most broadly applicable, misincorporation at a variety of amino acids is required. Accordingly, the efficiency of misincorporation by 18 anti-codon mutants of the cysteine tRNA was investigated. Mutant misincorporator tRNAs were constructed as described in Methods and assayed for their ability to misincorporate cysteine at specified codons throughout the TIM sequence. The observed misincorporation levels varied over a fairly narrow range (Table 1), with the differences probably reflecting proofreading activity of the cysteinyl tRNA synthetase. Only the tRNA complementary to the serine codon AGC caused an obvious impairment in cell growth. Misincorporation appears to follow normal wobble base pairing rules[Stryer, L., Biochemistry (W. H. Freeman and Company, New York, ed. 4, 1996). For example, the Val[GAC] tRNA misincorporated cysteine equally well at GUC or GUU codons, but not at GUG or GUA codons (data not shown).

Figure 7:
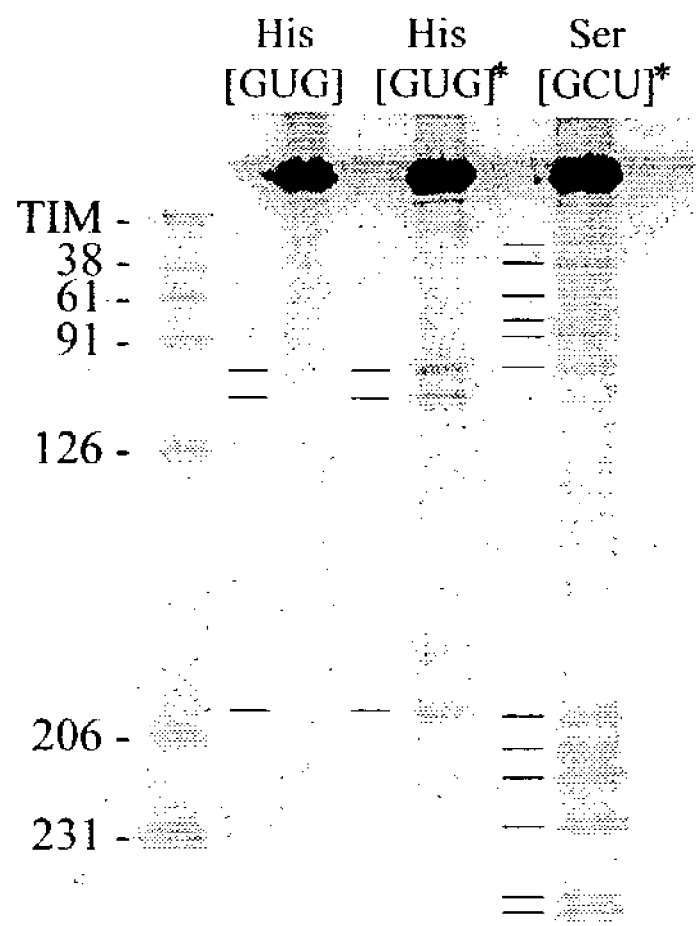
FIG. 7 is an autoradiograph of an electrophoretic gel showing the results of improved selection for misincorporation.

To expand the number of amino acids to which MPAX can be applied, we increased the misincorporation efficiency at serine and histidine codons using a genetic selection described previously (Doring V., P. Marliere P., Genetics 150:543, 1998). The selection was based on expression of the Helicobacter pylori amidase AmiE in E. coli. AmiE function is required for growth of E. coli with acetamide as the sole nitrogen source. Mutation of the essential catalytic residue C165 in AmiE eliminates enzymatic function (Kobayashi M., et. al., Biochemistry 31:9000, 1992). Therefore, efficient misincorporation by the appropriate misincorporator tRNA construct was required to restore the function of C165 mutants. For our studies, C165 was mutated to histidine or seine and co-transformed into E. coli with mutant misincorporator libraries. Variants were isolated from the library based on an increased growth rate in amine-free, acetamide-containing media. By direct biochemical measurement, some of these variants exhibit significantly higher levels of misincorporation (FIG. 7, Table 2). Isolation of mutants that efficiently misincorporate cysteine for serine and histidine residues suggests that it will be possible to select efficient misincorporator constructs for all 19 amino acids.

TABLE 2

Misincorporation Efficiency at Different Codons

| Amino Acid | Codon | Apparent Cleavage Efficiency* |
|---|---|---|
| Cys | UGC | 84.0% |
| Tyr | UAC | 1.9% |
| Ile | AUC | 0.7% |

TABLE 2-continued

Misincorporation Efficiency at Different Codons

| Amino Acid | Codon | Apparent Cleavage Efficiency* |
|---|---|---|
| Val | GUC | 0.7% |
| Leu | CUC | 0.7% |
| His (Selected) | CAC | 0.7% |
| Phe | UUC | 0.6% |
| Trp | UGG | 0.4% |
| Ser (Selected) | AGC | 0.4% |
| Asp | GAC | 0.3% |
| Ala | GCU | 0.2% |
| Arg | CGU | 0.2% |
| Thr | ACU | 0.1% |
| Asn | AAC | >0.1% |
| Gln | CAA | >0.1% |
| Glu | GAA | >0.1% |
| Gly | GGU | >0.1% |
| His | CAC | >0.1% |
| Lys | AAG | >0.1% |
| Pro | CCU | >0.1% |
| Ser | UCG | >0.1% |
| Ser | AGC | † |

*Average intensity of cleavage bands relative to the total protein.
† This tRNA construct is toxic in BL21(DE3) cells.

FIG. 7 is an autoradiograph of a electrophoresis gel showing the results of the selection for improved misincorporation. In FIG. 7, the misincorporation induced by genetically selected misincorporator tRNAs (His[GUG]*, Ser [GCU]*) is compared with the misincorporation induced by the original histidine misincorporator tRNA (His[GUG]). The parent serine misincorporator is not shown because it is toxic in BL21(DE3) cells. The expected cleavage pattern is shown as black lines to the left of each lane.

Example 5

High-Throughput Protein Footprinting Analysis

Although it is convenient to analyze MPAX data by SDS-PAGE, the gel readout requires that the protein of interest be devoid of native cysteine residues. To overcome this limitation, a mass-spectrometry method to measure the rate of alkylation at misincorporated cysteines was developed. The approach is based on a pulse-chase experiment that uses two protein labeling reagents of different isotopes, N-iodoacetyl, p-chlorobenzyl-12C6-glucamine and N-iodoacetyl, p-chlorobenzyl-13C6-glucamine. Except for the difference in nuclear isotope composition, the two compounds are chemically identical. One of the benefits of the isotopic protein labeling reagents of the present invention over other isotopic labeling reagents is that the starting material, 13C-glucose, is readily available and inexpensive. The boronate affinity purification is also efficient and significantly less expensive than biotin affinity purification.

Figure 8:
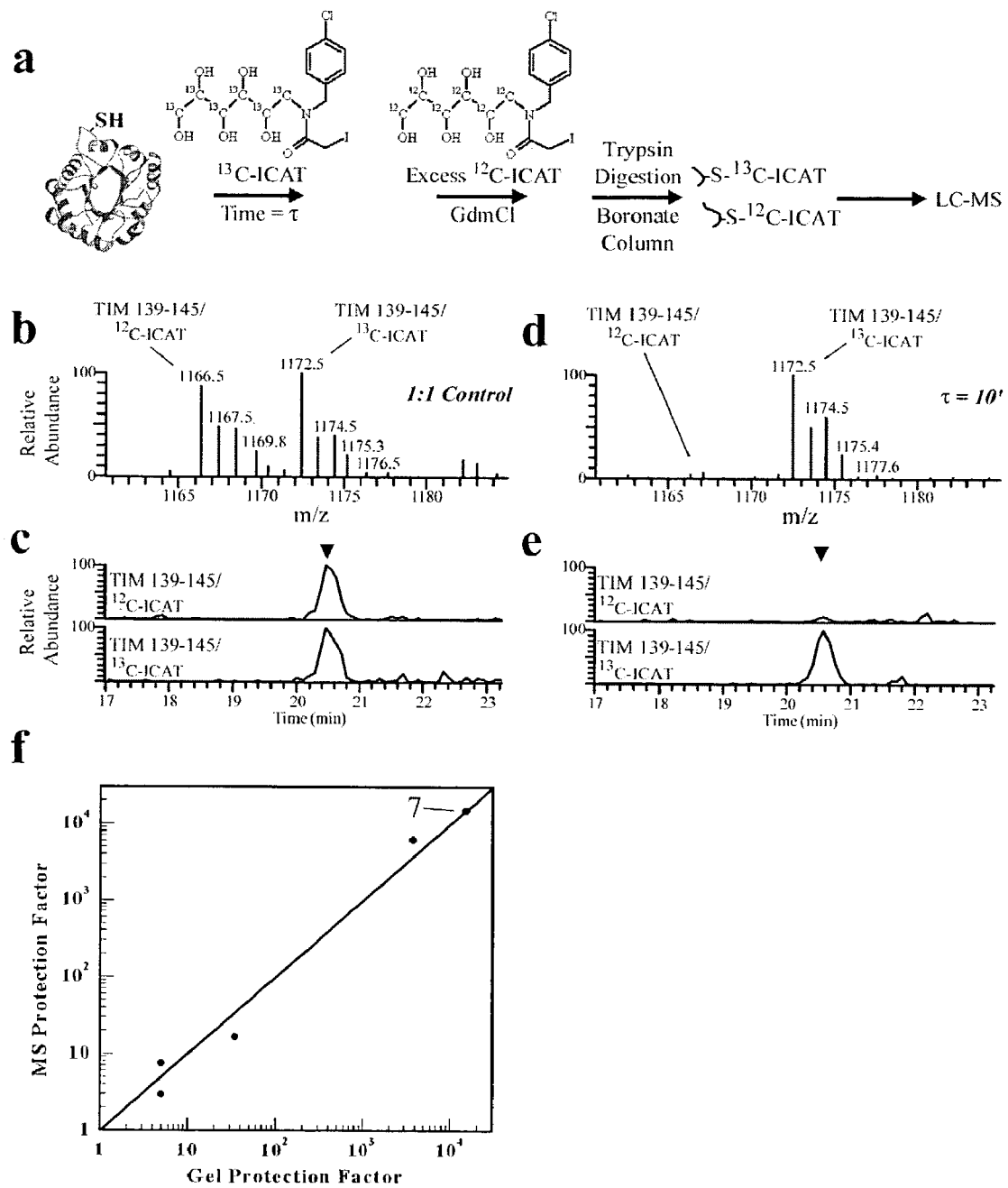
FIG. 8 includes panels A-F.

Labeling of misincorporated cysteines with CLR compounds. In this example, the protein was incubated for a variable time under native conditions with 13C-CLR, followed by incubation under denaturing conditions with an excess of 12C-CLR. FIG. 8, panel A is a schematic overview of the mass spectrometry readout method. The ensemble of cysteine-misincorporated proteins was alkylated for a variable time τ under native conditions with $^{13}$C-CLR. Excess $^{12}$C-CLR in 4 M guanidinium chloride (GdmCl) was subsequently added. Proteins were digested with trypsin, and peptides containing an alkylated cysteine were purified by affinity chromatography over polyacrylamide boronate resin, which serves as a capture reagent for the sugar group affinity tag. The affinity step takes advantage of the fact that the vicinal diols present in the glucose moiety of the CLR reagent bind to immobilized boronate groups (Liu, X. C., W. H. Scouten, *Methods Mol. Biol.* 147: 119, 2000). The purified peptides were analyzed by reverse-phase liquid chromatography coupled with mass spectrometry (LC-MS). Peptides were identified by their absolute mass and by their MS fragmentation pattern. The $^{13}$C-CLR:$^{12}$C-CLR ratio at each misincorporated cysteine determined the fractional alkylation that occurred during the initial alkylation pulse. Solvent-exposed cysteines were modified completely by $^{13}$C-CLR during the initial pulse, while buried cysteines were only alkylated with $^{12}$C-CLR upon unfolding of the protein in the chase step.

The $^{13}$C-CLR: $^{12}$C-CLR isotope ratio reports the fractional alkylation of the peptide during the initial alkylation pulse (FIG. 8, panels B-E). FIG. 7, panel B is a mass spectrum of a control experiment of a 1:1 mixture of $^{12}$C-CLR and $^{13}$C-CLR modified TIM peptide 139-145 [TLDVVER] containing cysteine misincorporated at L140. The calculated masses for the peptide [H$^+$-TC$^x$DVVER] where X indicates modification with either the 12C-CLR or 13C-CLR reagent are 1166.6 and 1172.6 Daltons respectively. The additional peaks at +1, +2, and +3 mass units correspond to naturally occurring chlorine isotopes that were used to aid peak identification. Mass chromatograms for the control experiment in FIG. 8, panel B are shown in FIG. 8, panel C. The abundance of peptides with mass 1166-1167 (upper) or 1172-1173 (lower) is plotted versus elution time from a reverse-phase C18 column. The arrowhead indicates the time that the mass spectrum shown in FIG. 7, panel B was taken. FIG. 7, panel D shows the mass spectrum of the modified TIM peptide 139-145[TLDVVER] (SEQ ID NO:1) prepared according to the scheme in (a) with τ=10 minutes. Mass chromatograms for the experiment shown in FIG. 8, panel D are shown in FIG.8, panel E. The abundance of peptides with mass 1166-1167 (upper) or 1172-1173 (lower) is plotted versus elution time from a reverse-phase C18 column. The arrowhead indicates the time that the mass spectrum shown in (d) was taken. Cysteine misincorporated at position 140 was completely alkylated by 13C-CLR in the initial alkylation pulse. The side chain of L140 was 40% solvent accessible in the native structure. Thus, the mass isotope ratios for cysteine-containing peptides provide a quantitative and site-specific measure of alkylation rates in the folded protein.

This example demonstrates the use of the CLR approach in measuring protection factors of misincorporated cysteines in the wild-type (cysteine-containing) TIM protein. Protection factors determined by mass spectrometry are in excellent agreement with those determined by gel methods (FIG. 8, panel F). FIG. 8, panel F is a plot of the protection factors measured by mass spectrometry readout versus those measured by gel readout. Data are shown in FIG. 8, panel F for nine leucine positions and the two naturally occurring cysteines. Seven data points overlap at the limit of resolution ($10^4$) in the upper right of the plot. The root mean square difference between the logarithms of the protection factors measured by the two methods is 0.15.

The use of mass spectrometry in the method of the invention provides a high-throughput readout that does not require the removal of native cysteines from the protein. The CLR detection method and the modular design of the misincorporation plasmids are well suited for proteome-wide studies.

Example 5

Measuring Local and Global Thermodynamic Stability with MPAX

Figure 15:
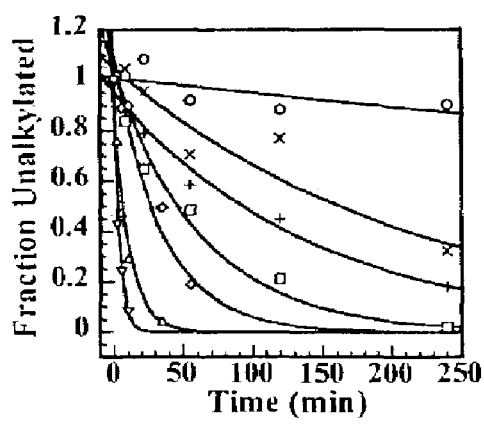
FIG. 15 is two graphs. The left hand graphs shows the rate of alkylation of C126 in 1.2 M (o), 1.4 M (x), 1.6 M (+), 1.8 M ( ), 2.0 M (( )), 2.2 M (Δ), or 2.4 M (V) guanidinium chloride (GdmCl). Solid lines are fits to a single exponential process. The graph on the right showslocal protein stability ($\Delta G_{N\_I}$) at C126 as a function of GdmCl concentration (calculated from the alkylation rates in (a).) The protection factor is equal to the equilibrium constant between folded and unfolded states when the rate of conformational closing is much faster than the rate of alkylation, a kinetic regime called EX2 in the hydrogen exchange literature. All alkylation rates were found to depend on the concentration of alkylating reagent, confirming that alkylation occurs by the EX2 mechanism.
Figure 15:
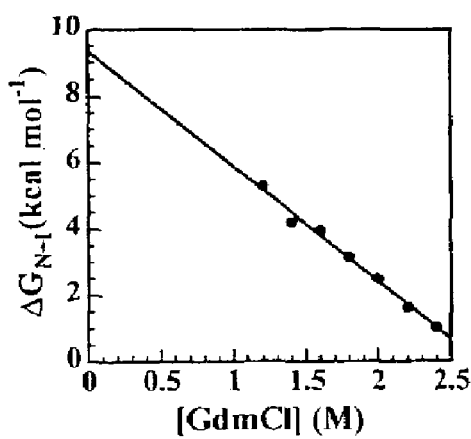

To carry out a native state exchange experiment using MPAX, we need to measure the local stability of TIM in the vicinity of each misincorporated cysteine probe. The relationship between local protein stability and measured cysteine protection factors is illustrated in FIG. 15. A cysteine probe buried in the protein structure reacts with a thiol-specific electrophile in solution only when it becomes exposed to solvent in an unfolded state. If refolding from the unfolded state is much faster than chemical modification of the cysteine probe (the EX2 limit1), then the protection factor for the cysteine probe is equal to the equilibrium constant for local unfolding. Recall that the protection factor is the factor by which native protein structure slows alkylation of a cysteine residue relative to the rate of alkylation of the same cysteine in the unfolded state. The free energy for local unfolding in the vicinity of a cysteine probe can be calculated directly from its protection factor as DGN->I=RT*ln{protection factor}.

To confirm that we could measure local protein stability using MPAX, we first measured protection at C126, a naturally occurring cysteine residue in TIM, as a function of guanidinium chloride concentration (FIG. C.2.a-1 NOTE: Please clarify reference to figure here—what figure number is this?|). TIM was incubated with the thiol-modifying reagent iodoacetamide in the presence of varying concentrations of denaturant, followed by cleavage of the protein backbone with 2-nitro-5-thiocyanobenzoic acid (NTCB) and separation of the cleavage products by gel electrophoresis. Alkylated cysteines are resistant to cleavage by NTCB. Thus, the loss of cleavage products at C126 over time reflects the rate of cysteine modification. The plot of local stability (DGN->I=RT*ln{protection factor}) versus guanidinium chloride concentration is linear. When extrapolated to zero denaturant concentration, the y-intercept corresponds to the free energy difference at 2 mM protein concentration between the native state and the partially or fully unfolded state that exposes C126 to solvent.

The measurement of an unfolding free energy for TIM represents a significant achievement. As is true of many proteins, the stability of TIM cannot be measured by spectroscopic methods because even moderate concentrations of the unfolded polypeptide aggregate. Stability can be ascertained from protection factors, however, because >99% of the protein remains folded under the native conditions used for the measurement (the 1% unfolded at any given time is detected). An implication of this result is that MPAX will be useful for measuring the thermodynamic stabilities of other large and poorly folding proteins.

Example 6

Detecting Protein Subdomains that Change Conformation Cooperatively

Figure 16:
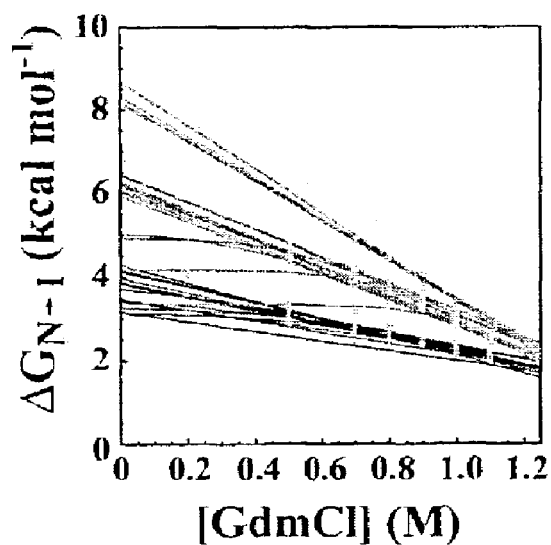
FIG. 16 is a graph (left panel) and a schematic (right panel) showing local stability of TIM. (left) Plot of GN_I for cysteine residues misincorporated at isoleucine, leucine, and valine positions in the C41V/C126A TIM background. (right) Residues in the crystal structure of TIM are grey-scaled according to their m-value.
Figure 16:
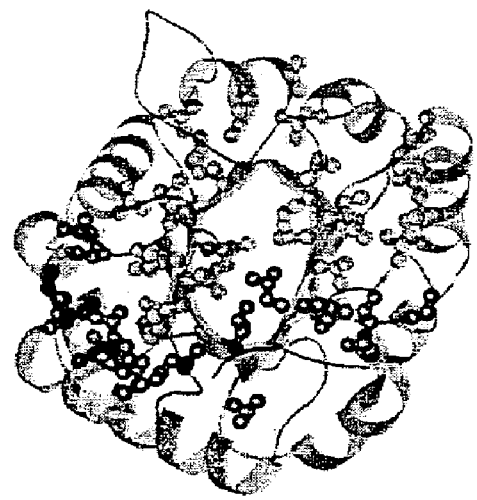

To identify cooperatively unfolding domains within the TIM structure, the alkylation rate of 61 cysteine probes misincorporated at isoleucine, leucine, and valine positions was determined as a function of guanidinium chloride concentration. Forty-six probes showed significant protection due to protein structure, in accordance with their level of solvent exposure in the crystal structure. A two-regime exchange model incorporating both local structure fluctuations (LSFs) and subdomain unfolding was used to fit the observed alkylation rates of all cysteine probes (FIG. 16). The m-values and extrapolated stabilities of the misincorporated cysteines cluster into three distinct isotherms. The values within each cluster are separated by more than two standard deviations from members of other clusters, confirming that the groups are distinct. The locations of misincorporated cysteines in each isotherm also cluster within the protein structure showin in FIG. 16.

Example 7

Mapping Intermediates in a Protein Folding Pathway

The presence of three isotherms indicates that there are at least three distinct intermediates in the equilibrium unfolding pathway of TIM. We refer to the three states as I1, I2, and I3 in order of increasing DGN->I. Since the native state of TIM is a dimer, a first step in characterizing the structures of these intermediates is to determine whether they are dimers or monomers. If an intermediate, I, were a dimer, increasing protein concentration would alter the stability of the native and I states equally, and no change in DGN->I would be observed. If I were a monomer, however, the native state would be stabilized relative to I by an increase in protein concentration, resulting in an apparent increase in DGN->I. Alkylation rates were measured at TIM concentrations of 1 mM and 5 mM. DGN->I for all intermediates was found to increase by 0.8±0.2 kcal mol-1 with a five-fold increase in protein concentration, indicating that all three intermediates are monomers.

Figure 17:
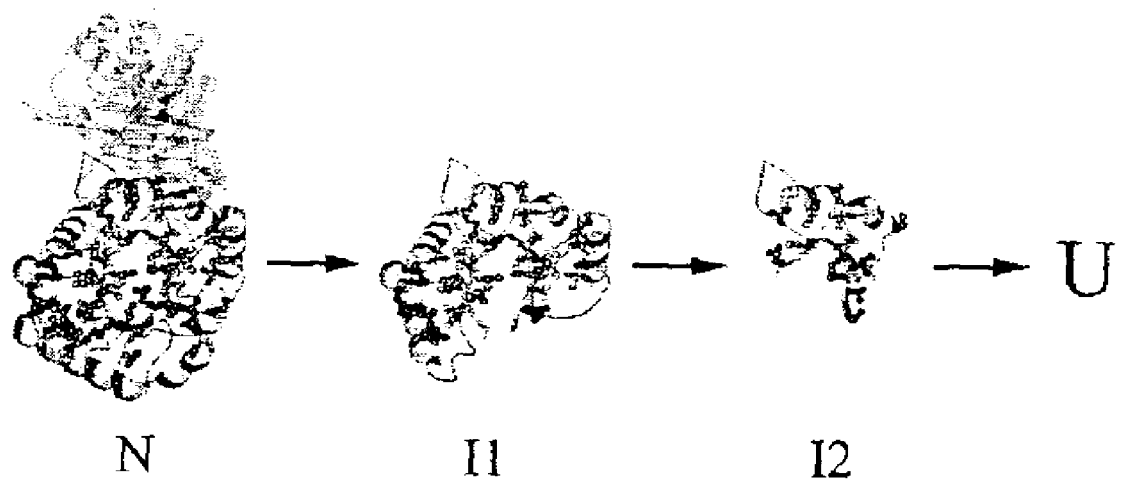
FIG. 17 schematically represents a sequential unfolding pathway for TIM.

The three intermediates may be arranged in a sequential pathway, three parallel pathways, or some combination of the two. In addition, one of the intermediates may or may not represent global protein unfolding. To distinguish between these possibilities, we determined the extent to which each alpha helix in TIM is unfolded in the I1, I2, and I3 intermediates by a mutational experiment based on MPAX stability measurements. Helices 6, 7, and 8 were observed to be unfolded in I1, I2, and I3. In contrast, helices 1, 4, and 5 were observed to be folded in I1, but unfolded in both I2 and I3. Finally, helices 2 and 3 were observed to be folded in I1 and I2, and unfolded in I3. All of the probes in each subdomain produced similar DGN->I and m-values in the mutant proteins, confirming that the subdomains unfold cooperatively. This analysis shows that when the one domain unfolds, other domains are already unfolded. Thus, I3 must represent global unfolding of the protein. Furthermore, one domain remains folded when another unfolds. Finally, the data show that the one domain can unfold independently of the other domains. The data support a model in which TIM unfolds along a sequential pathway: N->I1->I2->U (FIG. 17).

Example 8

Protein Footprinting in *Saccharomyces Cerevisiae*

Cysteine misincorporation may be used in yeast for footprinting approaches in vivo, or in crude cell-free extracts. To enable such methods, a series of yeast plasmids that direct efficient misincorporation of cysteine for each of the nineteen non-cysteine amino acids is created. These plasmids arecompatible with two complete yeast ORF expression libraries (the GeneStorm collection and the ExClones collection).

A parental misincorporation plasmid is constructed and shown in FIG. 14. The plasmid expresses the cysteine tRNA under an inducible promoter, and the cysteine tRNA synthetase under a constitutive promoter. Thirty-one mutant anti-codon triplets are introduced into the cysteine tRNA by Kunkel mutagenesis$_2$, and the misincorporation efficiency of each is measured biochemically using yeast triosephosphate isomerase as a model protein. Plasmids that fail to misincorporate cysteine efficiently are mutagenized, and subjected to selection in yeast for increased misincorporation efficiency.

Two strategies are pursued. The first, and simplest, strategy transplants functional misincorporator tRNA/cysteinyl tRNA synthetase pairs from *E. coli* into yeast. Cysteine misincorporator plasmids may also be made from scratch, using the yeast synthetase and tRNA as starting materials.

Suitable yeast misincorporator plasmid are based on the Invitrogen YES vectors (Invitrogen, Carlsbad Calif.). The YES vectors are a collection of plasmids that allow modular substitution of replication origins (to control copy number) and selectable markers. To construct a misincorporator vector, the bacterial (or yeast) cysteine tRNA is subcloned into the HindIII and EcoRI sites of pYES3/CT. The bacterial (or yeast) steinyl tRNA synthetase is PCR amplified with a primer that prepends a TEF1 promoter. This PCR fragment is subcloned into the EcoRI and PmeI sites of the pYES3/CT derivative above, to generate the vector yMPAX (FIG. 14).

The yMPAX plasmid contains two parallel transcriptional units. The inducible GAL1 promoter will drive transcription of the misincorporator tRNA when galactose is substituted for glucose as the carbon source in the growth medium. The constitutive TEF1 promoter will drive transcription of the cysteinyl tRNA synthetase under all conditions. Both transcriptional units read into the CYC1 transcriptional terminator. yMPAX has a high copy number replication origin, so that the misincorporator tRNA will be produced in large quantities after induction. Third, yMPAX contains an f1 phage replication origin, which will allow preparation of single stranded plasmid for site-directed mutagenesis.

Finally, yMPAX contains the TRP1 marker for auxotrophic selection, so it is compatible with the GeneStorm expression ORF collection (which uses the URA3 marker) and the ExClones expression ORF collection (which uses the LEU2 marker). Mutant anti-codon triplets will be introduced in the yMPAX plasmid by Kunkel mutagenesis. The resulting misincorporator vectors will be named YMPAX [ABC] where ABC denote the anti-codon sequence of the tRNA.

To evaluate cysteine misincorporation efficiencies, we subclone our his-tagged and protein kinase A epitope-tagged triosephosphate isomerase gene into the HindIII and PmeI sites of pYES2. This vector is cotransformed into the yeast stain INVSc1 with the yMPAX[ABC] vector of interest, followed by selection for growth on minimal glucose media deficient in uracil and tryptophan. Protein expression and misincorporation is induced by substituting glucose for galactose in the growth medium. The triosephosphate isomerase protein is affinity purified by nickel-NTA chromatography, and radioactively labeled with protein kinase A and $\gamma_{-33}$P-ATP. The efficiency of protein cleavage with 2-nitro-5-thiocyanobenzoic acid is measured as described in previous sections using bacterially expressed triosephosphate isomerase as a positive control.

If necessary, a selection scheme based on the function of the yeast thymidylate synthase gene (CDC21) is established to improve the cysteine misincorporation efficiency of yMPAX[ABC] vectors. Functional thymidylate synthase is required for growth of yeast on thymidine free media[37]. Thymidylate synthase contains an active site cysteine (C198) that becomes covalently bonded to the dUMP substrate during catalysis, and is necessary for enzymatic activity. This selection system is made using the yeast CDC21 expression plasmid from the GeneStorm collection, and changing the C198 codon triplet to an appropriate alternate triplet by Kunkel mutagenesis. The yMPAX[ABC] plasmid with the complementary anti-codon is mutagenized by irradiation with ultraviolet light, and cotransformed with the mutant CDC21 expression vector into yeast strain S288C (BY4736)-Δcdc21. S288C(BY4736)-Δcdc21 contains a complete CDC21 deletion and is deficient for TRP1 and URA3.

Transformants are selected for rapid growth on thymidine free media. Cysteine misincorporator plasmids that efficiently mistranslate the mutant codon at position 198 of the thymidylate synthase gene produce functional proteins, and these colonies grow faster than their siblings. To optimize the selection scheme, we replace the high copy number replication origin of the GeneStorm CDC21 plasmid with aCEN6/ARSH4 origin, which maintains the plasmid at one copy per cell.

A plasmid for use in other expression systems, such as baculovirus expression systems, and mammalian expression systems may also be designed using the above strategy, and used in these systems to misincorporated cysteins into proteins of interest.

Example 7

MSX

Protein conformational changes, including protein folding, signal transduction of ligand binding, the physical movements of molecular motors, and cyclical synthetic processes such as transcription and translation may be studied using MSX.

The fastest reaction of cysteine side chains is disulfide bond formation with thiosulfonates, which occurs with a second order rate constant of ~$8 \times 10^{-5}$ $M^{-1}S^{-1}$ at pH 9. At 10 mM thiosulfonate concentration, the half-life for disulfide bond formation is 87 microseconds. Thiosulfonate modification of single cysteine residues introduced into myoglobin by site-directed mutagenesis has been used previously to study its folding kinetics. Our second specific aim is to develop a millisecond footprinting technique, MSX, to detect thiosulfonate modification of cysteine residues introduced into proteins by parallel cysteine misincorporation.

MSX utilizes a pulse-chase protocol identical to the one described in for MPAX, except that a rapid quench-flow mixing instrument is required, and thiosulfonate reagents are substituted for iodoacetamide reagents. In order to match the modification rates of the pulse and quench reagents, both must contain a thiosulfonate functional group. We develop two sets of reagents, one that can be read out on gels, and a second that can be read out by mass spectrometry. For the gel readout, the pulse and quench thiosulfonate reagents are distinguished by the presence or absence of a glucose affinity tag (compound 11 and MMTS in FIG. 12). For the mass spectrometry readout, the pulse and quench thiosulfonate reagents are distinguished by their nuclear isotope composition (compounds 11 and 12 in FIG. 12).

Figure 13:
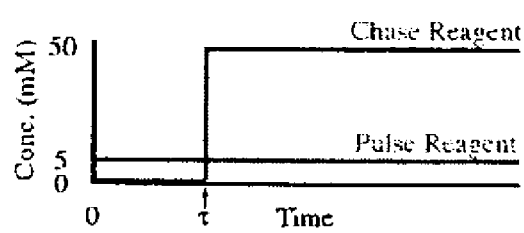
FIG. 13 is two graphs showing results from continuous and delayed pulse experiments.
Figure 13:
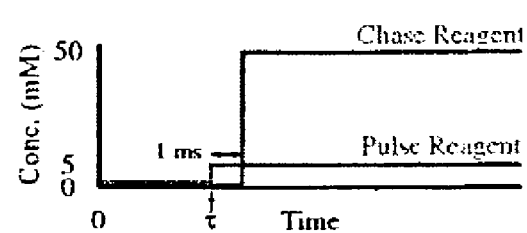

Two MSX protocols, a continuous pulse protocol and a delayed pulse protocol, are used (FIG. 13). For continuous pulse experiments, protein at pH 9 is mixed 1:1 with 20 mM thiosulfonate pulsereagent at time 0 in a quench flow instrument (KinTek, Philadelphia Pa.). At time τ, the reaction is mixed 1:1 with 100 mM thiosulfonate chase reagent. This continuous pulse protocol measures the time required for each cysteine to become solvent accessible.

For the delayed pulse experiment, the biological process under study is initiated at time 0 by mixing protein at pH 9 with a suitable diluent. At time τ, the reaction ismixed 1:1 with 20 mM thiosulfonate pulse reagent. After one millisecond, the reaction is quenched by 1:1 mixing with 100 mM thiosulfonate chase reagent. Because the half-life for disulfide bond formation with 10 mM thiosulfonate is 87 microseconds, a one millisecond pulse corresponds to ~10 modification half lives. Thus, a cysteine probe will be >50% modified if structure slows its reactivity by less than ten-fold, and less than 50% modified if structure slows its reactivity by more than ten fold. The one millisecond pulse essentially measures which probes are protected by more than ten-fold at time τ of a conformational process.

The sample preparation and analysis for MSX experiments closely follows the protocols developed for MPAX. For gel MSX experiments, MTSAG is used as the pulse reagent and MMTS as the quench reagent. The rapid mixing steps are performed with radioactively labeled protein. Following rapid mixing, samples are precipitated with trichloroacetic acid to remove excess thiosulfonates. Phenylboronic acid beads are added in batch to the resuspended protein. After one half hour, the supernatant is decanted. This process will remove proteins containing misincorporated cysteine residues that were modified with MTSAG in the pulse step, because MTSAG binds tightly to boronate beads. The protein remaining in the supernatant is treated with DTT, cleaved with 2-nitro-5-thiocyanobenzoic acid at misincorporated cysteines, and the fragments will be separated by SDS-PAGE as described. The extent of alkylation of each misincorporated cysteine at time τ is reflected by the fractional loss of radioactivity in the corresponding band of the developed gel.

For mass spectrometry MSX experiments, $_{13}$C-MTSAG is used as the pulse reagent and MTSAG as the quench reagent. Following rapid mixing, proteins will be worked up and analyzed exactly as described for MPAX experiments. Peptides are identified by their mass and fragmentation pattern. The extent of alkylation of each misincorporated cysteine at time τ is reflected by the $_{13}C/_{12}C$ ratio in the corresponding peptide product.

Data is usually interpreted by plotting the extent of alkylation at each misincorporated cysteine residue as a function of time τ. For continuous pulse experiments, the data will usually fit to a single exponential. To verify that modification occurs in the EX1 kinetic limit, we verify that the measured rates of alkylation are independent of the thiosulfonate concentration in the pulse step. The rates at which cysteine probes become solvent accessible, as measured by continuous pulse experiments, are used to determine the rate of formation of intermediates during conformational changes. Data from delayed pulse experiments will be fit to more complex functional forms that will depend on the problem being studied. For example, probes that are inaccessible at time zero and at long timepoints, but are transiently accessible to modification at intermediate timepoints could be observed.

The MSX technique is used to remeasuring the structure and rate of formation of a known intermediate in the folding pathway of bacterial ribonuclease H. The structure of the intermediate has been determined by independent means. It forms in less than 12 milliseconds, and folds to the native state with a first order rate constant of $0.45_{S-1}$ [34]. Ribonuclease H refolding will be monitored by delayed pulse MSX, and unfolding will be measured by continuous pulse MSX.

Rates of formation of the I1, I2 and U states of TIM from the native state is measured using continuous pulse MSX. This data completes our knowledge of the unfolding energy landscape for a $(\beta/\alpha)_8$ barrel protein (including the stabilities of intermediates and the nature of the transition states), and demonstrates the utility of MSX for the study of large proteins.

Example 8

MXLINK: Pairwise Residue Proximity for Structure Determination

MXLINK provides comprehensive surface residue proximity data. Using translational misincorporation, the surface of a protein is systematically covered with cysteine residues. The extent of coverage in a given sample is controlled by choosing the misincorporator tRNA's that are present during protein expression. On average, a single cysteine substitution is produced in each molecule. Thus, surface cysteines can be modified quantitatively without the concern that over-modification will grossly alter protein conformation. The misincorporated and modified cysteines are crosslinked to neighboring residues, and the crosslinks are detected by mass spectrometry. MXLINK is useful for determining the structures of proteins in complex mixtures, for determining the structures of difficult proteins (proteins impossible to crystallize and too large for NMR), and for high-throughput structural genomics work. Intermolecular crosslinks formed during MXLINK experiments aid in mapping interaction surfaces.

The method involves making intramolecular crosslinks between misincorporated cysteines and adjacent residues in a folded protein, isolating the crosslinked peptides after proteolysis of the protein, and to identifing the crosslinks by mass spectrometry. Usually, crosslinkers must be sufficiently nonspecific to generate abundant crosslinks, but sufficiently specific to provide interpretable data. The crosslinker may contain an affinity tag, so that crosslinked peptides can be separated from excess uncrosslinked fragments. The crosslinker should have relatively small dimensions, so that only short-range crosslinks will form. Optionally, a suitable crosslinker should be designed to cleave break (i.e. cleave in two) in a mass spectrometer, so that the masses of the two crosslinked peptide fragments can be measured independently. Finally, the crosslinker should be water soluble, it should fly well in a mass spectrometer, and it should be inexpensive.

As discussed above, the number and placement of misincorporated cysteine residues is controlled by the conditions used for protein expression. Misincorporated cysteines may be modified specifically either by alkylation or by disulfide bond formation. In an exemplary embodiment, suitable methods involve alkylation with α-halo amides, since this reaction is very specific, efficient, and irreversible. The chemistry used to form the second covalent bond (i.e. the "crosslinking bond") to the protein determines the number of crosslinks that are generated. One strategy utilizes a crosslinker that incorporates a perfluoroarylazide (crosslinker 1 in FIG. 10). The nitrene generated upon ultraviolet irradiation of the azide inserts nonspecifically into carbon-hydrogen bonds, and crosslinks to any other amino acid residue. The efficiency of perfluoroarylazide insertion into proteins is reported to exceed 80%. Another strategy utilizes a crosslinker that incorporates an active ester. This molecule only crosslinks to proximal lysine residues. The reactivity of the active ester is adjusted so that lysine residues are modified by an intramolecular mechanism, after prior alkylation of a nearby cysteine. Both crosslinkers incorporate a glucose affinity tag, and can be purified using commercially available phenylboronic acid resin. Both crosslinkers also incorporate a secondary amide. This design feature is based on the empirical observation that X-proline peptide bonds in proteins fragment far more efficiently than any other type of bond. Thus, both crosslinkers fragment in the mass spectrometer before the peptides to which they are attached fragment. A further crosslinker suitable for MXLINK methods is shown in FIG. 11.

MXLINK experimental protocols will closely follow the protocol used in MPAX examples above. Cysteine misincorporated protein will be alkylated for two minutes with 10 mM compound 1 or 10 mM compound 2. This short incubation modifies only surface cysteine residues, whose reactivity is not slowed by burial inside the protein structure. The protein is desalted over a G25 spin column (Amersham Pharmacia Biotech, Piscataway N.J.) to remove crosslinker that is not covalently attached. For experiments with compound 1, the sample is irradiated for 30 minutes with a handheld ultraviolet lamp to induce intramolecular nitrene insertions. For experiments with active ester-containing crosslinkers, the sample is incubated for several hours to allow intramolecular peptide bond formation between lysine side chains and the acyl imidazole in the crosslinker.

The samples are then digested to completion with a protease, as described above. Sequencing grade trypsin, proteinase K, thermolysin and pepsin may be used for this purpose. Crosslinked fragments are purified over phenyl boronic acid acrylamide resin as described above. Finally, the purified peptide fragments are analyzed on an MS/MS device, such as a ThermoFinnigan capillary LC/MS LCQ instrument using automated MS/MS detection. In the automated MS/MS mode, peaks of one mass eluting from the capillary are dynamically selected, collected in the quadrapole ion trap, fragmented, and remassed to determine the fragment molecular weights.

The deconvolution of large mass spectrometry data sets into identified peptide fragments and crosslinks is accomplished using automated software provided by ThermoFinnigan, and others. Construction of three-dimensional protein models from the crosslinking data may be done using Rosetta structure prediction software. Rosetta has the capacity to incorporate distance constraint information, so provision of crosslinking data is all that is required.

Triosephosphate isomerase (TIM) is characterized using MXLINK. Using site directed mutagenesis, mutant TIM proteins are constructed that have single cysteine substitutions at surface positions 131, 167 and 236. These mutants should produce a simple and predictable set of fragments when subjected to the MXLINK protocol with crosslinkers I and II, and other crosslinkers. Following these tests, we carry MXLINK studies on wild-type TIM protein expressed in the presence of isoleucine, leucine or valine misincorporator tRNA's. The misincorporated proteins contain distributed cysteine substitutions, and are used to test the feasibility of parallel data collection and analysis. We have performed extensive MPAX experiments with these molecules, and we are intimately familiar with their behavior. Finally, the crosslinking constraints derived from MXLINK are fed into Rosetta, and the structure of yeast TIM is predicted and compared to the known crystal structure. Because of its size and extensive beta sheet content, the TIM conformation can not be predicted by Rosetta without experimental constraints. We will assess how the extent of experimental data impacts the accuracy of the predicted models.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention described herein.

What is claimed is:

1. A method for analysis of protein structure, the method comprising:
  i. producing a modified protein by co-expression of:
    a) a polynucleotide encoding a mutant cysteinyl tRNA comprising an altered anticodon for misincorporation of a cysteine residue,
    b) a cysteinyl tRNA synthetase, and
    c) a polynucleotide encoding a protein of interest,
  wherein said co-expression results in production of a modified protein having a misincorporated cysteine residue;
  ii. providing for folding of the modified protein;
  iii. contacting the folded modified protein with a sulfhydryl-reactive compound under conditions suitable for modification of a solvent accessible cysteine residue in the modified protein; and
  iv. identifying reacted cysteine;
  wherein reaction of the sulfhydryl-reactive compound with the misincorporated cysteine residue indicates that the residue is solvent accessible.

2. The method of claim 1, wherein the polynucleotide encoding the protein of interest is modified prior to coexpression to remove or replace native cysteine residues.

3. The method of claim 1, wherein the sulfhydryl-reactive compound alkylates said solvent accessible cysteine residue in the modified protein.

4. The method of claim 3, wherein said compound is a halo amide.

5. The method of claim 4, wherein said compound is iodoacetamide.

6. The method of claim 1, wherein the sulfhydryl-reactive compound modifies said solvent accessible cysteine residue via a disulfide bond.

7. The method of claim 6, wherein said sulfhydryl-reactive compound is a thiosulfonate.

8. The method of claim 1, wherein said folded protein comprising misincorporated cysteine residues is reacted with a sulfhydryl-reactive compound and then subjected to proteolytic cleavage to make protein fragments.

9. The method of claim 8, wherein said proteolytic cleavage is done by a chemical or enzymatic agent.

10. The method of claim 9, wherein said chemical agent is chosen from cyanogen bromide and 2-nitro-5-thiocyanobenzoic acid (NTBC).

11. The method of claim 9, wherein said enzymatic agent is chosen from trypsin, chymotrypsin, proteinase K, thermolysin and pepsin.

12. The method of claim 8, wherein said protein fragments are detected by gel electrophoresis or mass spectrometry.

13. A method for analysis of protein structure, the method comprising:
  contacting a folded modified protein with a sulfhydryl-reactive compound, wherein the folded modified protein contains misincorporated cysteine residues, wherein the folded modified protein is produced by:
    co-expression in a recombinant host cell of a polynucleotide encoding a mutant cysteinyl tRNA comprising an altered anticodon for misincorporation of a cysteine residue, a cysteinyl tRNA synthetase and a polynucleotide encoding a protein of interest,
  wherein said co-expression results in production of a modified protein having a misincorporated cysteine residue;
  folding of the modified protein to produce a folded modified protein;
  said contacting being under conditions suitable for modification of a solvent accessible cysteine residue in the modified protein; and identifying reacted cysteine residues
  wherein reaction of the sulfhydryl-reactive compound with the misincorporated cysteine residue indicates the residues is solvent accessible.

* * * * *

UNITED STATES PATENT AND TRADEMARK OFFICE
CERTIFICATE OF CORRECTION

PATENT NO. : 7,288,382 B2  Page 1 of 1
APPLICATION NO. : 10/388963
DATED : October 30, 2007
INVENTOR(S) : Pehr A. B. Harbury It is certified that error appears in the above-identified patent and that said Letters Patent is hereby corrected as shown below:

On the Title page of the patent under INID Code (74):

- Attorney, Agent, or Firm: Please replace "Carole L. Francis" with --Carol L. Francis--.

In The Claims:

- In column 52 line 36: Please replace "residues" with --residue--.

Signed and Sealed this

Sixth Day of January, 2009

JON W. DUDAS
*Director of the United States Patent and Trademark Office*

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Thr Leu Asp Val Val Glu Arg
 1               5

<210> SEQ ID NO 2
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 2
cggactagac ggattgtcaa tccgctacat a                                      31

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 3
gtttctttga ttattgtcga tgatggaaac tac                                    33

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
ttcctttcgg gctttgttag c                                                 21

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
gacagcgcac aatgagttct g                                                 21